US008946499B2

(12) United States Patent
Iyer et al.

(10) Patent No.: US 8,946,499 B2
(45) Date of Patent: Feb. 3, 2015

(54) SYSTEMS, METHODS AND MATERIALS FOR DELIVERY AND DEBONDING ON DEMAND

(75) Inventors: Pradeep Iyer, Hacienda Heights, CA (US); Eugene Rozenbaoum, Pasadena, CA (US); David N. Edwards, Pasadena, CA (US); Prakash Mallya, Sierra Madre, CA (US); Tien Ly, Rosemead, CA (US)

(73) Assignee: Avery Dennison Corporation, Glendale, CA (US)

( * ) Notice: Subject to any disclaimer, the term of this patent is extended or adjusted under 35 U.S.C. 154(b) by 372 days.

(21) Appl. No.: 13/318,187

(22) PCT Filed: Apr. 27, 2010

(86) PCT No.: PCT/US2010/032610
§ 371 (c)(1),
(2), (4) Date: Oct. 31, 2011

(87) PCT Pub. No.: WO2010/129299
PCT Pub. Date: Nov. 11, 2010

(65) Prior Publication Data
US 2012/0123220 A1      May 17, 2012

Related U.S. Application Data

(60) Provisional application No. 61/172,956, filed on Apr. 27, 2009, provisional application No. 61/223,557, filed on Jul. 7, 2009.

(51) Int. Cl.
*A61F 13/00*      (2006.01)
(52) U.S. Cl.
USPC ............................................. 602/41; 602/42

(58) Field of Classification Search
USPC ......................... 602/41–54; 442/381; 428/103
See application file for complete search history.

(56) References Cited

U.S. PATENT DOCUMENTS

| 3,998,654 | A | 12/1976 | Falaas et al. |
| 4,324,595 | A | 4/1982 | Kasprzak |
| 4,472,480 | A | 9/1984 | Olson |
| 4,584,192 | A | 4/1986 | Dell et al. |
| 4,842,577 | A | 6/1989 | Konno et al. |
| 4,867,981 | A | 9/1989 | Grof |

(Continued)

FOREIGN PATENT DOCUMENTS

| WO | WO 96/25469 | 8/1996 |
| WO | 02/095655 | 11/2002 |

OTHER PUBLICATIONS

International Search Report dated Sep. 5, 2012 for International Application No. PCT/US2010/032610 filed Apr. 27, 2010.

(Continued)

*Primary Examiner* — Michael A. Brown
(74) *Attorney, Agent, or Firm* — Avery Dennison Corporation

(57) ABSTRACT

Various systems, methods and materials are disclosed that enable efficient delivery of an agent into an adhesively adhered article, in which the agent elicits a desired outcome, on demand. This strategy, though general in scope, is also more specifically described with regard to enabling painless or atraumatic removal of products adhering to mammalian tissues such as skin and hair by suitably exploiting the ingress of an appropriate agent or like fluid. Other techniques and articles that aid in the handling or removal of such adhesive products are also disclosed.

68 Claims, 15 Drawing Sheets

(56) References Cited

U.S. PATENT DOCUMENTS

| | | | |
|---|---|---|---|
| 4,917,112 A | 4/1990 | Kalt | |
| 4,987,893 A | 1/1991 | Salamone et al. | |
| 5,004,502 A | 4/1991 | Ramzan | |
| 5,032,637 A | 7/1991 | Therriault et al. | |
| 5,103,812 A | 4/1992 | Salamone et al. | |
| 5,156,911 A | 10/1992 | Stewart | |
| 5,183,841 A | 2/1993 | Bernard | |
| 5,336,207 A | 8/1994 | Norcia | |
| 5,385,965 A | 1/1995 | Bernard et al. | |
| 5,387,450 A | 2/1995 | Stewart | |
| 5,412,035 A | 5/1995 | Schmitt et al. | |
| 5,636,643 A | 6/1997 | Argenta et al. | |
| 5,645,081 A | 7/1997 | Argenta et al. | |
| 5,725,491 A | 3/1998 | Tipton et al. | |
| 5,803,639 A | 9/1998 | Gusakov et al. | |
| 5,843,018 A | 12/1998 | Shesol et al. | |
| 5,990,199 A | 11/1999 | Bealing et al. | |
| 6,045,895 A | 4/2000 | Hyde et al. | |
| 6,107,219 A | 8/2000 | Joseph et al. | |
| 6,191,338 B1 | 2/2001 | Haller | |
| 6,368,687 B1 | 4/2002 | Joseph et al. | |
| 6,436,227 B1 | 8/2002 | Adler | |
| 6,495,229 B1 | 12/2002 | Carte et al. | |
| 6,503,231 B1 | 1/2003 | Prausnitz et al. | |
| 6,541,098 B2 | 4/2003 | Venkatasanthanam et al. | |
| 6,610,762 B1 | 8/2003 | Webster et al. | |
| 6,630,049 B2 | 10/2003 | Hannington et al. | |
| 6,794,318 B2 | 9/2004 | Anderson et al. | |
| 7,078,582 B2 | 7/2006 | Stebbings et al. | |
| 7,270,861 B2 * | 9/2007 | Broering et al. | 428/35.7 |
| 7,332,205 B2 | 2/2008 | Hannington et al. | |
| 7,344,618 B2 | 3/2008 | Hannington et al. | |
| 7,354,889 B2 | 4/2008 | Askill et al. | |
| 7,396,976 B2 | 7/2008 | Hurwitz et al. | |
| 7,399,800 B2 | 7/2008 | Burch | |
| 2001/0043943 A1 | 11/2001 | Coffey | |
| 2002/0034913 A1 * | 3/2002 | Curro et al. | 442/381 |
| 2002/0039867 A1 * | 4/2002 | Curro et al. | 442/373 |
| 2002/0164446 A1 | 11/2002 | Zhou et al. | |
| 2006/0030808 A1 | 2/2006 | Kennedy | |
| 2007/0054821 A1 | 3/2007 | Askill | |
| 2007/0154670 A1 | 7/2007 | Hannington | |

OTHER PUBLICATIONS

Written Opinion dated Sep. 5, 2012 for International Application No. PCT/US2010/032610 filed Apr. 27, 2010.

J. Moffatt, P.J. Franks, H. Hollingworth, Position document, European Wound Management Association (EWMA) London, UK Medical Partnerships Ltd. p. 1-17, 2002.

"Skin Irritation Due to Repetitive Application of Adhesive Tape; the Influence of Adhesive Strength and Seasonal Variability", F. Tokumura; K. Umekage; M. Sado; S. Otsuka, S. Suda; M. Taniguchi; A. Yamori; A. Nakamura; J. Kawai; K. Ika, Skin Research and Technology, 11, 102-106 (2005).

"Using Protective Skin Wipes Under Adhesive Tampes", Dealy C., J., Journal of Wound Care Jul./Aug., vol. I, No. 2, 1992.

* cited by examiner

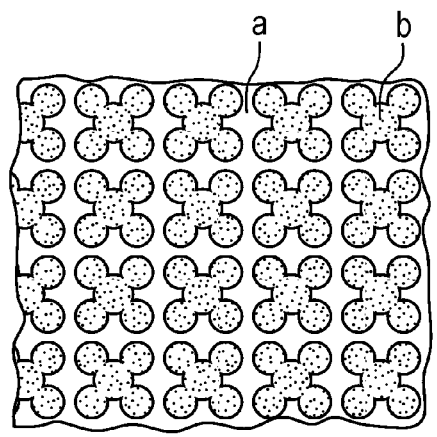
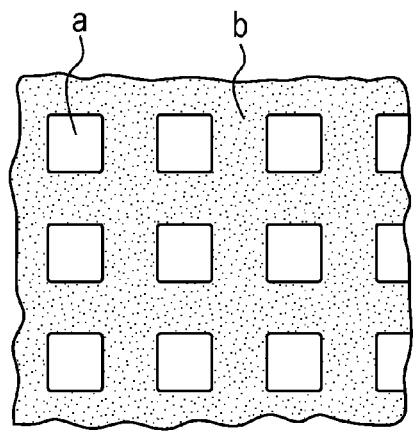
FIG. 26A          FIG. 26B
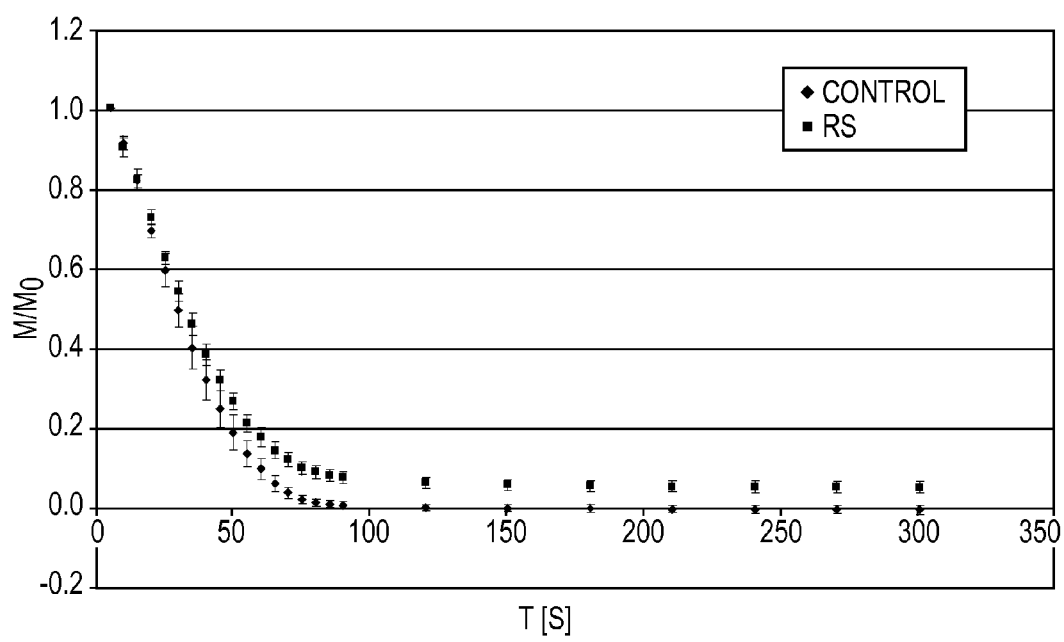
FIG. 27

SYSTEMS, METHODS AND MATERIALS FOR DELIVERY AND DEBONDING ON DEMAND

CROSS REFERENCES TO RELATED APPLICATIONS

The present application is a 371 of International application No. PCT/US2010/032610, which was published in English on Nov. 11, 2010, which claims priority upon U.S. Provisional Application No. 61/172,956 filed Apr. 27, 2009, and U.S. Provisional Application No. 61/223,557 filed Jul. 7, 2009, all of which are incorporated herein by reference in their entireties.

FIELD OF THE INVENTION

The present invention relates to adhesively adhered articles such as adhesive tapes, bandages, wound dressings, etc., that attach securely to a given substrate and which can be easily and painlessly removed.

BACKGROUND OF THE INVENTION

Adhesives are widely used for securing a variety of articles to substrate(s). Pressure sensitive adhesives (PSA's), in particular, have been widely studied in an attempt to tailor their properties so that they readily "wet out" and bond rapidly to a given surface upon application of minimal pressure. Often, the goal is that articles carrying these adhesives eventually debond, with equal ease, from an underlying surface cleanly, i.e. without leaving any residue behind from either cohesive and/or facestock-adhesive interfacial failures. This objective entails balancing a number of seemingly contradictory properties at the adhesive interface including (i) optimizing the viscoelastic performance window of the adhesive, (ii) assessing the chemistry and solubility parameters of the adhesive components involved and whether they are single or multi-phase separated in nature, (iii) determining the extent of appropriate crosslinking, (iv) considering the conditions of bonding, e.g. pressure, surface roughness, etc, (v) assessing the application and dwell conditions of the adhesive, e.g. contact area and time, temperature, pressure, environmental conditions, etc., and (vi) addressing debonding modes between the adhesive and substrate, e.g. peel angle, speed, environmental conditions, etc.

Although adhesive debonding has been widely discussed and recognized to be an important challenge, few solutions have been achieved. The challenges associated with adhesive debonding are well recognized, as noted in "Pain at Wound Dressing Changes", C. J. Moffatt, P. J. Franks, H. Hollinworth, Position Document, European Wound Management Association (EWMA), London, UK Medical Partnerships Ltd., pages 1-17, 2002. Adhesive debonding and particularly, with ease and on demand, still presents a formidable technological hurdle.

A wide array of medical products are designed to attach securely to skin and to be retained thereto under a range of adverse conditions including contact with water, e.g. as may be encountered during bathing, swimming, etc.; contact with sweat, sebum or other body fluids; adhering to uneven or complex surface(s) associated with the skin or body that deform variably under mechanical stresses; exposure to heat, e.g. as may occur during a sauna; exposure to sunlight or other environmental factors; contact with other liquids such as hot or cold beverages; and/or being subjected to physical stresses resulting from motion such as during exercise. In view of these and other factors, adhesives for medical applications are typically engineered to adhere securely and for extended time periods to skin.

While many commercial products are known that purportedly facilitate removing an adhesively adhered article from a user's skin, there remains a critical and unmet need for ready, painless removal of the article, on demand, and without causing trauma. This need is particularly evident when adhesively adhered products are peeled off from the skin of elderly patients which is typically fragile and thin. In addition, a need exists for readily removable articles that can be used with children, cancer patients specifically those with skin cancer, premature babies that have skin that is not fully developed, those with diseases that have a severe impact on the skin, or sensitive skin.

"Switchable" Adhesives

Adhesives having selectable or "switchable" adhesion characteristics are known in the art. Temperature switchable adhesives utilize crystallizable moieties within the adhesive matrix that provide for temperature sensitive bonding and debonding. Representative examples of these types of adhesives are described in U.S. Pat. Nos. 5,156,911; 5,387,450; and 5,412,035 for example.

More recently, U.S. Pat. No. 7,399,800 describes utilizing appropriately modified tackifiers.

U.S. Pat. No. 6,610,762 describes the use of post UV polymer crosslinking of a pressure sensitive adhesive to reduce peel strength for easy debonding.

U.S. Pat. No. 5,032,637 describes pressure sensitive adhesives that can be inactivated upon exposure to water by using water soluble tackifiers.

U.S. Pat. No. 7,078,582 exploits the utility of elastic deformation to enable easy removal of medical tapes. This approach is similar to that utilized by certain commercially available products containing adhesives known in the art under the designation "Command" adhesives.

Adhesive Removal in Medical Applications

A prime application of selectively releasable or variable adhesion adhesives, is in the medical field. Among the most common techniques for facilitating adhesive removal or debonding involve contacting the adhesive with various readily available fluids such as (i) oils, (ii) solvents such as isopropyl alcohol, acetone, etc. or (iii) an adhesive removal aid such as Uni-Solve available from Smith & Nephew, Niltac™, or Hollister Medical adhesive remover #7731, etc.

U.S. Pat. No. 4,324,595 describes a method for removing tacky adhesives and articles attached using such adhesives, such as pressure sensitive adhesives in bandages, surgical tape and the like. The method involves applying a volatile methylsiloxane fluid to the tacky adhesive and then removing the bandage or tape from the underlying substrate. The '595 patent specifically notes that the methylsiloxane fluid is applied to the articles and allowed to permeate therethrough to reach the adhesive interface.

U.S. Pat. No. 4,867,981 is directed to tape releasing compositions for separating pressure sensitive adhesive tapes or bandages from an underlying surface. The patent describes that upon application of the composition, the fluid permeates through a porous layer (of the tape or bandage) to the adhesive material, "thereby abating the bonding force".

Although satisfactory in certain regards, frequent issues exist when using such crude methods such as dispensing inconsistent amounts of adhesive removal fluids, poor distribution of the fluid, need for subsequent clean up, collateral damage or stain to adjacent clothing, and potential harm to the injury site by rubbing or application of pressure, etc. Furthermore, artisans have recognized the importance in attempting to balance the chemistry of the ingredients of adhesive removers in order to enable rapid penetration of the adhesive bulk without unduly compromising its cohesive integrity.

Recognizing these and other deficiencies, artisans have continued to attempt to provide improved techniques and compositions enabling selective removal of adhesively adhered articles. Many of these attempts focused on improving the efficacy of the adhesive removal agent.

Specific examples from the patent literature include the following. U.S. Pat. No. 5,336,207 discloses the use of rubbing oxyalkene ether and liquid hydrocarbons to help remove medical adhesives from the skin.

U.S. Pat. No. 5,004,502 describes the use of non-irritating detackifying agents.

US Patent Application Publication 2007/0054821 A1 discloses the utility of tetrahydrofurfuryl acetate for effective removal of medical adhesives. That publication also calls for "rubbing the remover on the surface in order to enhance removal".

U.S. Pat. No. 6,436,227 discloses the use of soaking a tape for at least two minutes with limonene to remove adhesive bandages.

None of the previously noted art overcomes the inherent inefficiency of the delivery method of the adhesive removal agent. This is particularly critical when dealing with impermeable devices or systems. U.S. Pat. No. 5,803,639 recognizes this hurdle. However, that patent attempts to overcome the challenges associated with delivery of an adhesive removal agent by devising a special scraping tool to peel an adhesively adhered article from its edges, and thereby expose the adhesive. An adhesion reducing fluid is then administered under the article.

Others have devised an array of different devices and articles that purportedly facilitate adhesive debonding. U.S. Pat. No. 5,843,018 describes the use of a disposable sterile emollient carrier device to treat simple and complex cutaneous injuries by utilizing an elongated non-adhesive wrap around various body parts to attach or detach when needed.

U.S. Pat. No. 6,191,338 discloses a bandage design that minimizes pain from pulling hair during bandage removal.

U.S. Pat. No. 7,396,976 describes an easy to peel bandage construction that contains a plurality of pockets or microcapsules of an adhesive-inactivating ingredient. The microcapsules can be ruptured on demand by application of pressure to enable easy peel off. Premature rupturing is a distinct disadvantage of this approach.

3M and Coloplast have commercial products such as Cavilon™ #3343 (also known as No Sting Barrier Film) or Prep Protective Skin Barrier products like Duoderm. However, these products represent attempts to simply pre-coat the skin prior to adhesive contact to minimize trauma and skin erythema. In this regard, see Dealy C., J. Wound Care, 1, 19 (1992).

Many patents describe low trauma adhesive chemistries utilizing hydrogels, hydrocolloids, soft silicone gels, formulations with aiding additives, etc. However, these strategies often result in inadvertently compromising one or more other desirable properties such as maintaining initial adhesion levels, causing undesirable moisture vapor transmission rate(s) (MVTR) and/or oxygen transmission rate(s) (OTR), or resulting in other unwanted characteristics, etc. Since good adhesion and easy debonding are intrinsically conflicting properties, it is difficult to simultaneously achieve both of these aspects. And, it is exceedingly difficult to accomplish both of these objectives without compromise of other important adhesive properties.

Accordingly, despite the numerous and varied attempts of prior artisans, a need remains for a strategy by which an adhesively adhered article may be easily and painlessly removed from a user's skin, without causing trauma and without any detrimental effects upon the adhesive or the article prior to removal. More particularly, a need remains for an article, system, method and materials for achieving this unique feature.

SUMMARY OF THE INVENTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

The previously noted difficulties and drawbacks are overcome and remedied by the present apparatus, systems, and methods for multilayer laminates that can be adhesively adhered to a substrate such as skin, and subsequently readily removed.

In one aspect, the present invention provides a multilayer laminate that is adherable to a substrate and selectively releasable therefrom upon application of an adhesive deactivating agent to an outer face or perimeter of the laminate and appropriate contacting between the agent and the adhesive. The laminate comprises an interior layer defining a plurality of fluid passageway conduits extending through the interior layer. The interior layer exhibits a controllable flow profile across the thickness of the interior layer. The interior layer defines a bottom surface and an oppositely directed top surface. The laminate also comprises an adhesive layer disposed along the bottom surface of the interior layer. And, the laminate comprises a cover layer disposed on the top surface of the interior layer. Upon contacting the adhesive layer to the substrate, the laminate is adhesively adhered thereto. Upon removal of the cover layer from the laminate, the interior layer and plurality of fluid passageway conduits are exposed. And, upon application of an effective amount of the adhesive deactivating agent to the top surface of the interior layer, transport of the agent to the adhesive, and sufficient contact time between the agent and the adhesive and more particularly along the bonding interface, the adhesively adhered laminate can be easily removed from the substrate.

In another aspect, the present invention provides a system for selectively adhering and selectively releasing a multilayer laminate to and from a substrate. The system comprises a multilayer laminate that includes an interior layer defining a plurality of fluid passageway conduits extending through the interior layer. The interior layer exhibits a controllable flow profile across the thickness of the interior layer. The interior layer defines a bottom face and an oppositely directed top face. The laminate also includes an adhesive layer disposed along the bottom face of the interior layer. And, the laminate further includes a cover layer disposed on the top face of the interior layer. The system also comprises an adhesive deactivating agent. Upon contacting the adhesive layer to the substrate, the laminate is adhesively adhered thereto. Upon removal of the cover layer from the laminate, the interior layer and plurality of fluid passageway conduits are exposed. After applying an effective amount of the adhesive deactivating agent to the top face of the interior layer, transport of the agent through the layer via the plurality of passageways to the adhesive, and sufficient contact time between the agent and the adhesive, the adhesively adhered laminate can be easily removed from the substrate.

In yet another aspect, the present invention provides a method for selectively adhering and removing a multilayer laminate to and from a substrate. The method comprises providing a multilayer laminate comprising (i) an interior layer defining a plurality of fluid passageway conduits or apertures extending through the interior layer, the interior layer exhibiting a controllable flow profile across the thickness of the interior layer, the interior layer defining a bottom surface and an oppositely directed top surface, (ii) an adhesive layer disposed along the bottom surface of the interior layer, and (iii) a carrier or cover layer disposed on the top surface of the interior layer. The laminate also includes a (iv) release liner in contact with the adhesive layer. The method also comprises contacting the adhesive layer of the laminate to the substrate, to thereby adhere the laminate to the substrate. This is preferably performed by removing the release liner from the adhesive layer of the laminate to thereby expose the adhesive layer. The laminate is then applied onto the substrate. And, the method further comprises selectively releasing the adhesively adhered laminate from the substrate by removing the cover layer therefrom to expose the top surface of the interior layer, applying an effective amount of the adhesive deactivating agent to the top surface of the interior layer so that the agent travels through the fluid passageway conduits defined in the interior layer and thereby contacts the adhesive layer disposed along the bottom surface of the interior layer, and allowing sufficient contact time between the adhesive deactivating agent and the adhesive so that the adhesively adhered laminate can be easily removed from the substrate.

In a further aspect of the presently described invention, a method for selectively adhering and selectively releasing a multilayer laminate to a substrate and wound bed utilizing a vacuum assisted closure therapy is described and includes the steps of initially providing a multilayer laminate comprising (i) an interior layer defining a plurality of fluid passageway conduits or apertures extending through the interior layer, the interior layer exhibiting a controllable flow profile across the thickness of the interior layer, the interior layer defining a bottom surface and an oppositely directed top surface, (ii) an adhesive layer disposed along the bottom surface of the interior layer, (iii) a carrier layer disposed on the top surface of the interior layer, and (iv) a release liner in contact with the adhesive layer. The method includes placing a portion of thick material that is sized and cut over the wound and peeling off the release liner from the adhesive layer of the multilayer laminate. Next, the multilayer laminate is applied over a wound bed such that the carrier layer is disposed on the top surface of the interior layer of the multilayer laminate. A hole is cut in the multilayer laminate and a pad is applied over the hole in the multilayer laminate. The pad is preferably a pad assembly adapted for vacuum connection such as used in vacuum assisted closure therapy and may include associated tubing, clamp, and connector. A preferred example of such a pad is a T.R.A.C. pad available from KCI Licensing, Inc. A vacuum source is connected to the pad. After use, the multilayer laminate is treated with an adhesive deactivating agent to facilitate removal of the pad. The pad releases along with the outer layer cover layer.

In a yet still further aspect of the presently described invention, a kit for use in wound care applications is described and includes a multilayer laminate, an adhesive to apply the laminate to a surface, a vacuum port for use with the laminate, and an adhesive deactivating agent for removing the laminate from the surface.

In still another aspect of the invention, a multilayer laminate is provided. The multilayer laminate is adherable to a substrate and selectively releasable therefrom. The laminate comprises a film layer, an adhesive layer, and a controlled infraction layer, the infraction layer defining a face for contacting a substrate for adherence thereto. The infraction layer selectively exhibits at least one of (i) a disrupting characteristic and (ii) dissolving upon exposure to an adhesive deactivating agent.

And in a further aspect, the present invention provides an assembly for depositing printed ink conduits on a target layer. The assembly comprises a low surface energy layer defining an exposed face, and a printed ink conduit pattern disposed on the face of the low surface energy layer, the pattern having characteristics for controlling fluid flow properties therethrough.

As will be realized, the present invention is capable of other and different embodiments and its various details are capable of modifications in numerous respects, all without departing from the invention. Accordingly, the drawings and description are to be regarded as illustrative and not restrictive.

BRIEF DESCRIPTION OF THE DRAWINGS

These, as well as other objects and advantages of this invention, will be more completely understood and appreciated by referring to the following more detailed description of the presently preferred exemplary embodiments of the invention in conjunction with the accompanying drawings, of which:

FIG. 26 schematically illustrates two types of samples that were used in various investigations.

FIG. 27 is a graph illustrating improved fluid ingress and retention times of a preferred embodiment laminate.

DETAILED DESCRIPTION OF THE EMBODIMENTS

Figure 1:
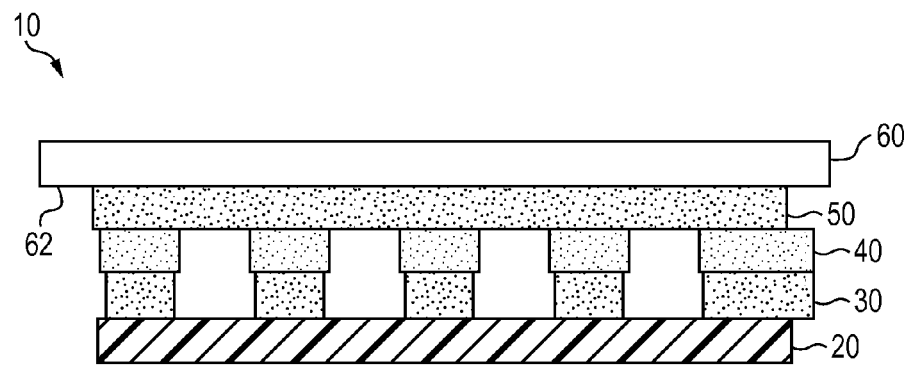
FIG. 1 is a schematic illustration of a preferred embodiment laminate in accordance with the present invention.

The present invention is now illustrated in greater detail by way of the following detailed description which represents the best presently known mode of carrying out the invention. However, it should be understood that this description is not to be used to limit the present invention, but rather, is provided for the purpose of illustrating the general features of the invention.

A significant feature of the present invention involves efficiently enhancing the ease of an adhesive debonding process with the aid of an agent that is introduced, only when needed. This allows for much greater freedom in designing a laminate such as a face/adhesive/release system, to ensure other necessary properties are robustly maintained. For example, excessive skin adhesion levels may occur that can eventually cause pain during removal. This is explained in the Test Methods section presented herein. This phenomenon can be eliminated or at least significantly reduced if debonding of the adhesive from the skin is efficiently aided by the ingress of an appropriate agent into the laminate expressly for removal purposes. The delivery of the debonding agent is focused towards rapidly and controllably disseminating the agent particularly, though not exclusively, into the bonding interfacial area.

Another significant feature of the present invention is the provision of a laminate having at least one layer specifically designed to control the passage of a liquid or flowable agent therethrough in an expeditious manner. Many of the previously noted patents described in the Background section herein, rely upon ingress of an adhesive removal fluid along the edges or lateral regions of a bandage or dressing largely via capillary action. Similarly, for the several noted patents that describe applying a fluid to the top of a dressing or medical tape, those strategies rely upon having the appropriate solubility parameter aided penetration efficiency to readily "soak" through one or more layers for fluid transport. None of these strategies are effective, particularly when one or more layers is occlusive in nature and/or for relatively large adhesive interface surface areas.

It is well recognized by medical practitioners that the etiology of dermal peel related pain perception is complex and depends on a number of factors well beyond peel adhesion values. One such factor is the concomitant stripping of corneocytes, i.e. surface skin cells, induced by the mechanical peeling of an adhesive. This is discussed in the Test Methods section herein. Administration of an agent designed to specifically mitigate this just prior to a planned removal can thus be extremely beneficial. Other pain mitigating agents may also be advantageously and simultaneously introduced at or proximate the adhesive interface including but not limited to anesthetics, cooling/warming agents, anti-histamines to minimize irritation, and/or special coating agents that minimize hair pulling, etc.

Delivery, on demand, of many other beneficial agents is also contemplated. Examples include, but are not limited to, agents that cause or promote sterilization such as by chemical means, radiative means, etc. Analytics, on demand, are also contemplated for diagnostic monitoring of important parameters such as temperature, histamine/heparin levels, signs of infection, erythroedema (a sunburn like rash), etc., especially by taking advantage of the available laminate structures engineered especially, although not exclusively, within the peri-wound area. Additional examples of agents that can be delivered on demand include agents for immediate or on demand delivery of medicaments directly to the peri-wound skin to alleviate various medical conditions such as inflammation, allergy, pain, etc. Delivery of any one or combinations of these is made less onerous by the elegant and effective use of this present invention.

Multilayer Laminates

A preferred embodiment in accordance with the present invention features a "sandwiched" multiple layered construction as depicted in FIG. 1. This preferred embodiment comprises a release liner along the bottom face of the laminate; a co-continuous skin-friendly pressure sensitive adhesive layer which ensures an air seal; a perforated polyurethane interior layer to allow fluid ingress; a generally continuous "removable" pressure sensitive adhesive layer disposed on a top face of the interior layer; and a top layer having appropriate properties such as a suitable moisture vapor transmission rate (MVTR), desired optical properties, etc.

Specifically, schematically FIG. 1 illustrates a preferred embodiment 10 laminate in accordance with the present invention. The laminate 10 comprises a release liner 20, a layer 30 of an apertured pressure sensitive adhesive (PSA) typically utilized for applications involving contact with skin, an apertured interior layer 40 configured for selectively directing flow or transport of agent(s) to the layer 30, a layer 50 of a pressure sensitive adhesive that is removable with a cover layer 60. Each of these layers is described in greater detail herein. It will be appreciated that in no way is the present invention limited to this particular embodiment, its configuration, and/or materials. Instead, the present invention includes a wide range of other laminates, arrangements, and materials, as described in greater detail herein.

A significant feature of the present invention is the provision of an interior layer in the multilayer laminates described herein such as depicted as layer 40 in FIG. 1. That layer defines a plurality of conduits, apertures, perforations, slits, or other means that enable controlled passage of one or more agent(s), such as an adhesive deactivating agent, from one face of the layer through the thickness of the layer, to the other oppositely directed face of the layer. After having passed through the layer and to its other face, the agent(s) can then contact the adherend directly or travel further through the interface and/or laminate as desired.

In accordance with the present invention, the interior layer exhibits a controllable flow profile across the thickness of the interior layer. The term "controllable flow profile" as used herein refers to the arrangement, location, shape and configuration of the passageways or conduits extending through the interior layer. Preferably, although not necessarily, the shape and configuration of each passageway is maintained relatively constant across the thickness of the interior layer. This aspect provides significantly greater ability to control the transport characteristics of the agent (or an analyte as in the case of sensing elements) from one face of the layer to another face of the layer. Furthermore, this feature is readily distinguishable from prior art materials such as porous paper or fibrous layers in which void regions may extend from one face of the material to another face. In those materials, such intrinsic interior voids exhibit a great range of lengths, interior surface area, shapes, and configurations, all of which effect agent transport. Such widely varying voids makes controlling transport characteristics through the material suboptimal and seldom provide the desired control.

The size of the conduits or apertures defined in the interior layer of the preferred embodiment multilayer laminates may range from about 0.5 mils to about 2000 mils, preferably from about 1 mil to about 400 mils, and more preferably from about 10 mils to about 300 mils. These dimensions of aperture size are diameters for circular shaped apertures that potentially afford uniform fluid egress. For non-circular shaped apertures, these values represent effective diameters. It will be appreciated that the present invention includes sizes greater than or less than these sizes.

Furthermore, the conduits or apertures may all be of the same size or of different sizes. Depending upon the particular application and/or laminate structure, it may be desirable to form a collection of apertures of one size in particular location(s) in the interior layer, and form a collection of apertures of another size in other location(s) in the interior layer. Moreover, it is contemplated that only one or more portions of the interior layer may define apertures, and other portions be free of apertures. In this regard, it may be beneficial to define a collection of apertures in only a central portion of an interior layer and leave the remaining regions of the layer aperture free or vice versa.

The conduits or apertures may be in the form of nearly any shape, such as circular, square, rectangular, triangular, polysided, irregular, slit-shaped, etc. Again, the particular selection of aperture shape(s) or combination of shapes will depend upon the particular application and/or laminate structure. Alternatively, conduits may also comprise unique materials that selectively afford ready transport to matched fluidic agents.

The number of conduits or apertures defined in the interior layer may also vary. However, a typical number may be from about 5 to about 500, preferably from about 10 to about 250, and more preferably from about 20 to about 200 per square inch ($in^2$) of layer. It will be understood that the present invention includes the use of a greater or lesser number. It is also contemplated that the density of apertures, i.e. the number of apertures per unit of area of the layer, may vary at different locations along the layer. For example, it may be preferred for certain applications to provide for a relatively high aperture density within a particular region of the layer, and a lower aperture density in other regions. The present invention includes varying aperture density.

The selection of the size, shape, number of apertures, and aperture density defined in the interior layer determine the percentage or proportion of the surface area of the interior layer that permits passage of agent(s) or analyte therethrough. Generally, for many applications, the percentage of apertured surface area of the interior layer is at least about 10% and typically from about 10% to about 90%, preferably about 15% to about 85%, and most preferably from about 0% to about 80%. It will be understood that the present invention includes laminates utilizing interior layers having percentage openings greater than or lesser than these amounts. Furthermore, it is to be understood that the present invention includes interior layers having different aperture percentages along different regions of the layer.

Additional details of the preferred embodiment multilayer laminate illustrated in FIG. 1 are as follows. The top or cover layer 60 may be in the form of a polyurethane film having a thickness of about 0.5 mils. In certain embodiments, it may be desired to include one or more over-hanging edges 62 of the top film 60 to facilitate removal of the top film. Providing one or more over-hang tabs may serve as additional substrate for carrying indicia or for writing upon, promoting ease of removal of the top film when wearing gloves, and/or reduce accumulation of dirt or other residue along the edge regions of the laminate.

The release liner 20 serves to protect the adhesive and can be peeled off just prior to attaching the laminate 10 to a user's skin. While the liner will generally be non-perforated, it may optionally be perforated if so desired. Although a perforated middle or interior layer 40 is included in the preferred multilayer laminate, the top continuous pressure sensitive adhesive layer 50 assists in assuring controllable moisture vapor transmission rate (MVTR) characteristics without compromising peri-wound sealing efficiency. A co-continuous (e.g. where an adhesive may be patterned but still remain continuous) pressure sensitive adhesive layer 50 is particularly important in treating wounds using techniques like VAC™—vacuum assisted closures available from Kinetic Concepts, Inc. (KCI) of San Antonio, Tex. and as described in U.S. Pat. Nos. 5,636,643 and 5,645,081, or wound fluid flushing such as KCI's "Instill™" products.

As noted herein, the present invention is believed to be readily applicable for use in conjunction with vacuum assist (or assisted) closure (VAC) therapy, also known as negative pressure wound therapy (NPWT). Kinetic Concepts, Inc. (KCI) provides a wide range of products, systems, and methodologies for using VAC or NPWT. Vacuum assist closure therapy is based upon forming and maintaining a sub-atmospheric pressure about a wound area. Such reduced pressure has been found to provide numerous benefits such as helping to uniformly draw wounds closed, assisting granulation, helping to remove interstitial fluid to allow tissue decompression, helping remove infectious materials, and providing a beneficial healing environment.

Just prior to removing the adhesively adhered laminate, one can preferentially peel off the top film 60. This readily exposes a particular percentage or proportion of the underlying adhesive 30 and more importantly, the adjacent skin through a collection of perforations of the interior layer 40 or corresponding structure that is in direct contact with the skin or other adherents. In the case of vacuum assisted closure (VAC) therapy, top or cover films 60 should be optically transparent and highly conformable, and typically quite thin such as in the range of from about 0.2 to about 2 mils. However, as will be understood, the present invention includes layers 60 having thicknesses greater than or less than this preferred range. These films or layers 60 may optionally have supporting backing films that enable ease of applying such thin, conformable laminates. Once the top film is removed, the adhesive layer 30 and portions of the adherend are directly accessible through apertures/conduits defined in layer 40 and can then be readily treated with various agent(s) that can be tailored to quickly deactivate adhesion and promote easy removal of the laminate with minimal pain or trauma.

The present invention laminates as described herein can be incorporated in or used in conjunction with a wide array of medical products. Representative examples of such products include, but are not limited to bandages, dressings, gauze, tape and related products, wound closure products such as patches, covers and the like, closure strips foam padding, surgical tapes, and pads. As explained herein, numerous applications are contemplated in which the present invention laminates are incorporated in and/or used in conjunction with vacuum assist closure (VAC) products and therapies.

The present invention contemplates the selective administration of one or more agents into the multilayer laminates described herein. The agent(s) are introduced into the laminates by exposing the apertured interior layer of the laminate and administering the desired agent(s) onto a top face of that layer. Agents that can be beneficially introduced, on demand, into the laminate may include, but are not restricted to, beneficial additives such as anesthetics, analgesics, and cooling/heating agents, etc. Although a wide array of agents can be introduced into the laminates described herein, it is preferred that the agent(s) include at least one adhesive deactivating agent. Silicone or perfluoroalkyl derivatives are particularly effective in deactivating skin adhesives. Various adhesive deactivating agents are described in greater detail herein.

The application of the agent(s) can be made mess-free by delivering them through (i) secondary carrier devices such as by a spray, roll-on or brush-on container, (ii) individually sterile packed "wet wipe" dispensers, (iii) "skin barrier" like applications that deliver the agent especially from below and "skin over" applications for optimum retention, (iv) impregnated gauze/foam carriers, and/or (v) encapsulated "release-on-demand" mediums to precisely meter or measure out needed amounts. The shells rupture if the laminate is stretched or subjected to any sort of trauma releasing the adhesive deactivating agent allowing for easy removal of the laminate. The application of the agent(s) can also be accomplished by delivering them through channels incorporated in the adhesive layer of the multilayer laminate which allows for rapid ingress of an adhesive deactivating agent thus allowing for easy removal of the laminate. Many embodiments of the delivery system and methods may be engineered into the laminate system, e.g. the top cover layer may additionally carry encapsulated agents on the outside so that once it is peeled away, it can be reapplied while presenting the opposing face such and appropriated stimulated to induce delivery of the agent into the conduits contained within the inner laminate layers. One or more of these techniques allows for controlled mess-free sterile dispensation that can be tailored to work optimally for a given adhesive. Assuming that the dominant deactivating mechanism is interfacial bond fracturing, the total amount needed is expected to be quite meager and easy to handle.

The selection of one or more fluid agents is governed by considerations such as the agents being readily available, safe to use, diffuse/reach the skin interface efficiently, deactivate adhesion rapidly but not unduly compromise the adhesive and/or carrier film so as to cause cohesive failure to leave a mess, not unduly modify the skin surface so subsequent adhesion is less robust such as in leaving a low energy coating like silicone, and not cause allergic reactions or other adverse reactions.

The present invention laminates include nearly any combination of pervious or non-pervious pressure sensitive adhesive (PSA) layers, such as layer 30 in FIG. 1, and pervious or non-pervious backing assemblies having a layer providing controlled flow, such as layer 40 in FIG. 1. For example, in one aspect, the present invention includes a laminate comprising a pervious layer of a PSA and a pervious backing. In another aspect, the invention includes a laminate comprising a non-pervious layer of a PSA and a pervious backing. In another aspect, the invention includes a laminate comprising a pervious layer of PSA and a non-pervious backing. And, in another aspect, the invention includes a laminate comprising a non-pervious layer of PSA and a non-pervious backing. An example of a non-pervious backing is an occlusion laminate with a continuous facestock. An example of a non-pervious PSA is a conventional continuously coated adhesive. Examples of a pervious backing are perforated layers, non-woven materials, paper, cloth, etc. Examples of a pervious PSA include an open cell foam adhesive, microfibrous adhesives such as described in U.S. Pat. No. 6,368,687, perforated adhesive layers, adhesive layers defining embossed channels, patterned coatings of adhesives such as described in U.S. Pat. No. 6,495,229, and adhesives with one or more phases or materials that serve as conduits.

The adhesiveness of the present invention laminates can be increased through embossing of the adhesive through the multilayer liner. The embossing method may include placing a mesh between the liner and the adhesive, creating patterns in the adhesive. As a result, adhesive may now flow freely into the areas corresponding to the open area of the mesh increasing the coat weight of the multilayer laminate. Tests have shown that the peel adhesion almost doubles. Even though the adhesiveness increases, the laminate's removability ease after the application of an adhesive deactivating agent is unaffected.

Adhesiveness may also be increased by increasing the coat weight of the adhesive. However even though the adhesiveness decreases if using an adhesive deactivating agent such as HMDS (hexamethyldisiloxane) the adhesiveness of the laminate decreases to approximately $0.3 N/in^2$.

Even higher levels of adhesions of 90 or 120 gsm, decrease to approximately $0.3 N/in^2$ as soon as they are sprayed with HMDS (hexamethyldisiloxane)

The present invention laminates are preferably adapted to be adhered to a wide range of substrates. A prime example of such substrates is mammalian skin. Although human skin is likely the prime example of application of the invention, it is to be appreciated that the invention may also find use for application to skin and outer body surfaces of other animals. A wide array of uses is thus contemplated even more broadly than just the medical or veterinarian field. For instance the present invention can be used in the signage field, removing large adhesive laminates like retroreflective or graphics products made by the present assignee, for other non-medical areas that have a need for temporary bonding material such as semi-conductor assemblies, wall paper removers, bathroom enclosure fixtures, tire and wheel balancing weight with attachment and detachment assemblies, etc.

Example 1

Figure 2:
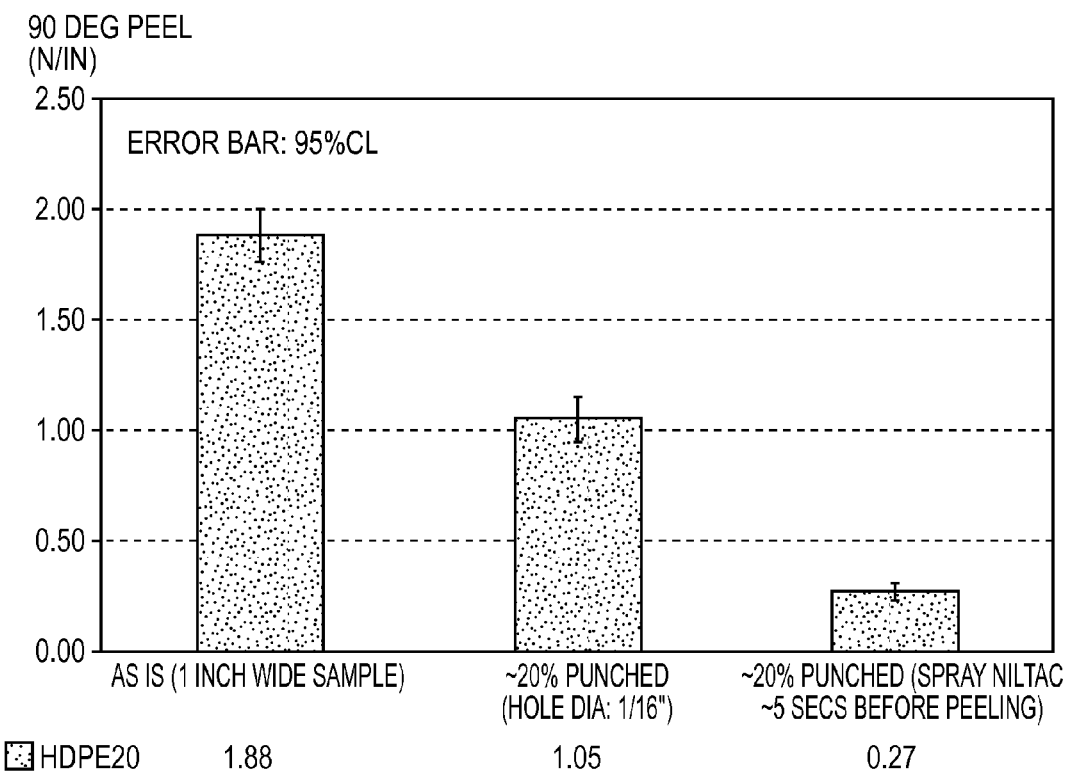
FIG. 2 is a graph illustrating peel strength measurements of several adhesively adhered layers and corresponding substrates.

An adhesively coated commercial product available from the present assignee under the designation "I-1827A" production laminate (a breathable transparent polyurethane (PU) film), was manually punched with approximately 63 perforations (average diameter of 1/16 inch) per square inch representing a removal of approximately 20% of the adhesive. FIG. 2 shows that the measured room temperature 90° peel adhesion on high density polyethylene (HDPE) substrates decreases to about 1 N/in$^2$ as compared to its original value of 1.9 N/in$^2$ when left non-perforated. When the laminate is sprayed with hexamethyldisiloxane (HMDS) and immediately, or at least within about 15 seconds, peeled, while still wet, the measured adhesion precipitously drops to approximately 0.3 N/in$^2$. The peel adhesion quickly restores back to about 1 N/in$^2$ if the peel measurement is made after the laminate is allowed to completely dry. Similarly, when using Nitac™ TR101, a "sting-free" medical adhesive remover available from Union Camp, the adhesively adhered article or strip must be peeled off when wet. If let to dry, the adhesive peel value would be similar to the peel value prior to application of Nitac™.

This unique behavior of a deactivating agent like HMDS is particularly noteworthy, since it is remarkably efficient in adhesive debonding when wet but quickly evaporates leaving minimal residue. This is particularly important since it is not always desirable to leave a low energy residue coating like silicone that can readily compromise subsequent adhesion to the same location on the skin, a practice often needed especially in the treatment of chronic and severe wounds that may require many days to heal. Many other agents can used to optimize or further promote this attribute.

Comparative Example

Spraying I-1827A laminate with HMDS results in no loss of peel strength in the absence of the perforations confirming the importance of designing an efficient delivery system for the agent.

Adhesive Deactivating Agents

The terms "adhesive deactivating agent" or "adhesive debonding agent" as used herein refer to any agent or combination of agents that serve to reduce and preferably eliminate an adhesive bond between an adhesive and a substrate, which as described herein is typically mammalian skin. The adhesive deactivating agent is typically in a fluid form and exhibits a viscosity at generally ambient conditions and other properties and characteristics such that the agent can travel through the various apertures in the multilayer laminates described herein and reach the adhesive and preferably at least a substantial portion of the adhesive interface.

An important class of compounds for use as the adhesive deactivating agent is silicones including methicones and dimethicone (also known as polydimethylsiloxane) derivatives such as Toray fluids available from Dow Chemical Corp., tetramethylsilane, hexamethyldisiloxane (HMDS) and their higher homologues. As noted, the adhesive deactivating agent may also include one or more perfluoroalkyl derivatives. Additional classes of components for use in adhesive deactivating agents include, but are not limited to low molecular weight oils; water with soap, pH modifiers, and/or containing other modifiers and ingredients; beneficial esters such as isopropyl myristate, triglyceryl caproates, tetrahydrofurfural acetate or other esters and alkyl esters; limonene derivatives; paraffinic solvents; hydrocarbon solvents; various alkyl ethers; aromatic esters, surfactants, agents typically used in facial/mascara remover chemistries; hair spray ingredients; dermal medicants/lotions; allergy/inflammation/anesthetic agents such as for example Dermaplast spray from Medtech and related agents; and combinations thereof. Additional examples of compounds suitable for use as the adhesive deactivating agent or for use in association with such agent are provided in U.S. Pat. Nos. 3,998,654; 5,004,502; 5,336,207; 6,436,227; and 7,354,889.

Particularly preferred silicones or rather polysiloxanes include, but are not limited to, dimethyl silicones or dimethylpolysiloxanes having the general formula $(-CH_3)_2-SiO)_x$, cyclic or straight chain, where x is a number of about 2 to several hundred. Trimethylsiloxy end-blocking units may be used for stabilization.

Figure 25:
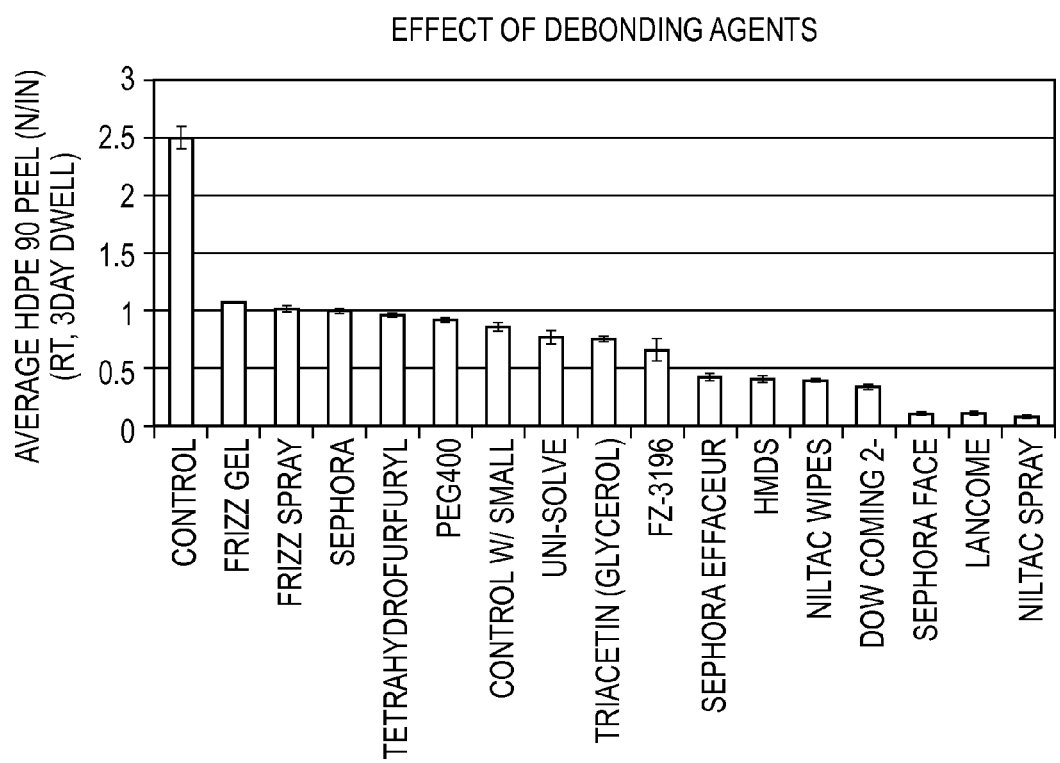
FIG. 25 is a graph of peel strength values for adhesively bonded samples after treatment with various debonding agents.

Choice of the agent is particularly important as depicted in Table 1 below which lists the relative effects of various adhesive debonding agents upon measured peel adhesions. Specifically, samples were adhesively bonded to a high density polyethylene (HDPE) substrate and allowed to dry for three days. Then, an effective amount of an adhesive debonding agent as listed in Table 1 was applied. The 90° peel force was then measured. The data of Table 1 is illustrated graphically in FIG. 25.

TABLE 1

Effects of Various Adhesive Debonding Agents

| Samples | Avg Peel (N/in) | 95% CL |
|---|---|---|
| Control | 2.4925 | 0.11 |
| frizz gel | 1.079 | 0.00 |
| frizz spray | 1.0305 | 0.01 |
| Sephora demaquillant | 0.999 | 0.04 |
| Tetrahydrofurfuryl acetate | 0.969 | 0.04 |
| PEG400 | 0.933 | 0.00 |
| Control w/small holes | 0.863 | 0.04 |
| Uni-Solve | 0.76 | 0.06 |
| triacetin (glycerol triacetate) | 0.7555 | 0.02 |
| FZ-3196 | 0.6575 | 0.09 |
| Sephora effaceur de maquillage | 0.4365 | 0.02 |
| HMDS | 0.4085 | 0.02 |
| Niltac Wipes | 0.3935 | 0.01 |
| Dow Corning 2-1184 | 0.325 | 0.02 |
| Sephora Face | 0.1025 | 0.02 |
| Lancome | 0.098 | 0.02 |
| Niltac Spray | 0.072 | 0.01 |

Regarding the various debonding agents listed in Table 1, most are self explanatory. The "frizz" products are commercially available hair care products. Sephora demaquillant is a makeup remover formulation available from Sephora USA, Inc. of San Francisco, Calif. PEG 400 is polyethylene glycol 400. Uni-Solve is available from Smith & Nephew. FZ-3196 is a volatile alkyl methyl siloxane fluid from Dow Corning. Sephora effaceur de maquillage is a commercially available composition for erasing makeup, from Sephora. HMDS is hexamethyldisilazide also known as bis(trimethylsilyl) amine. Dow Corning 2-1184 is a mixture of volatile linear polydimethylsiloxanes. Sephora Face is a formulation for completing makeup removal from Sephora. Lancome is a commercially available composition available under that designation.

It is contemplated that the present invention may also utilize one or more agents based upon chemistries that allow for coating hair, such as for example by coating with amino polydimethylsiloxane (PDMS) which may selectively adhere through quaternary amine salt formation with surface acid groups believed to be present from oxidation of cystine disulfides, or fluoro esters, etc. Such low energy coatings could then help ease or eliminate hair pull induced pain during peeling off or otherwise removing the adhesive product.

Other embodiments in accordance with the present invention include chemistries that can be appropriately combined with "switchable adhesive" technologies, for example using heat and/or water to help debond as described in U.S. Pat. Nos. 5,183,841 and 5,385,965.

Another example of an adhesive deactivating agent is a debonding agent of fugitive silicones. Additional adhesive deactivating agents come in many forms including but not limited to wipes and sprays that can be individually packed and/or provided in a sterile container. The adhesive deactivating agent can be applied in a variety of different ways and using a wide array of strategies and techniques. For example, the agent can be applied via a secondary carrier device. The agent can also be applied via a skin barrier-like application. The agent could also be applied via an impregnated gauze and/or foam carrier.

After administration of an effective amount of an adhesive deactivating agent onto an exposed face of the laminate, the agent travels or is otherwise transported to the vicinity of the adhesive interface along which bonding occurs between the laminate and the substrate such as a user's skin. Contact or exposure occurs between the deactivating agent and the adhesive which, as explained herein, results in a reduction or elimination of the previous adhesive bond. The amount of contact time between the agent and adhesive necessary to result in debonding depends upon a variety of factors namely relating to the composition and interaction between the agent and adhesive. However, it is contemplated that for many applications, sufficient contact may be from only several seconds up to several minutes. The present invention includes contact times shorter and longer than these representative times.

Not wishing to be bound to any particular theory, it is believed that delivering a deactivating fluid agent efficiently to the adherend—adhesive interface may well be a key factor that readily and rapidly compromises the interface. Several additional factors that may be important to maximize or further promote this desired outcome could include one or more of the following:

Molecular weight—small molecules are generally expected to exhibit higher levels of interfacial diffusion than larger ones.

Surface roughness of the adherend and adhesive surface—the rougher the interacting interface, the easier it may be for interfacial fluid ingress which is also expected to contribute towards lower initial peel adhesion levels.

Adhesive topology—voids, patterns and/or channels all will contribute to the efficiency of fluid delivery to the interface.

Adhesive chemistry—the nature of the adhesive and particularly with regard to its chemistry/solubility parameter(s), crosslinking, and phase structure are all important parameters.

Compatibility—the agent should be sufficiently compatible for favorable ingress through the laminate and to the interface, but not so compatible as to adversely compromise the adhesive bulk and cause cohesive failures that can potentially leave residue. Effective interaction with the substrate (e.g. skin chemistry, physiology and/or surface exudates) can be particularly important.

Pain Mitigation—mitigating the pain of removal by, perhaps, advantageously interacting with the skin surface to dissolve/weaken interfacial exudates or bonds, minimize irritation by suppressing release of histamines, coating hair to minimizing their pulling, changing the skin topology to allow for easier debonding, providing for a physiological or even psychological relief, such as for example through cooling, warming and or wetting sensations.

In certain applications, it may be preferred to utilize an adhesive deactivating agent which is a medicant or medicant-like anesthetic, analgesic, cooling and/or heating agent, or combinations thereof.

Additional Aspects

Figure 3:
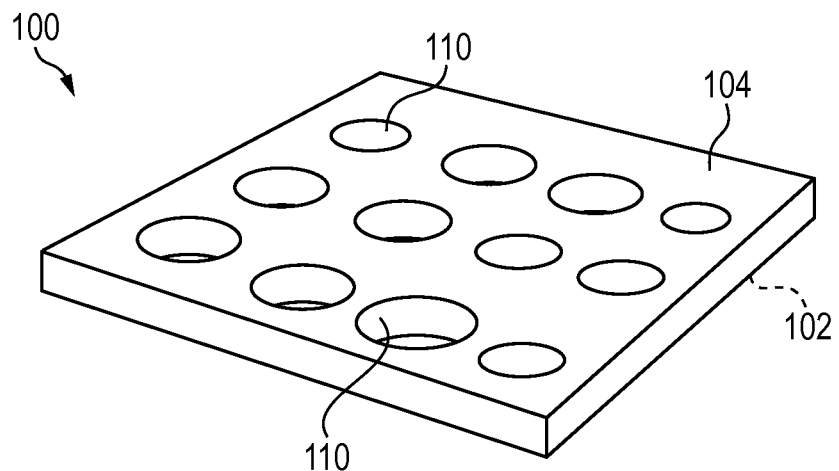
FIG. 3 is a schematic illustration of a preferred configuration for a layer having a collection of fluid passageways used in a multilayer laminate in accordance with the present invention.

The following figures illustrate various modes of action that potentially deliver the adhesive deactivating agent efficiently to the bonding interface. FIG. 3 is a schematic illustration of a preferred interior layer 100 that can be used as the interior layer 40 as shown in FIG. 1. The layer 100 defines a first face 102, a second oppositely directed face 104, and a plurality of conduits, apertures, perforations, openings, or wells 110 extending through the layer 100 and between the first and second faces 102, 104. The wells 110 in FIG. 3 represent the perforations or pores that allow rapid ingress of fluids through the adhesive system. These can be readily formed by mechanical techniques such as for example by use of magnetic rotary dies available from Rotometrics of Eureka, Mo., laser ablation such as by systems available from Preco of Lenexa, Kans., or other suitable means.

In another preferred embodiment in accordance with the present invention, the configuration or arrangement of perforations or apertures in the overlay, interior film such as layer 40 shown in FIG. 1, is matched with that of the adhesive, such as shown as layer 30 in FIG. 1. This configuration provides greater access and exposure of the adhesive interface for the adhesive deactivating agent. This configuration may result in shorter contact times between the adhesive deactivating agent and the adhesive.

In certain embodiments, it may be desirable that the overlay film or top cover such as shown as layer 60 in FIG. 1 be porous or composed of non-woven materials, etc. that freely allow fluid movement. These features may be readily implemented especially if optical transparency of the film and/or laminate is not critical.

Figure 4:
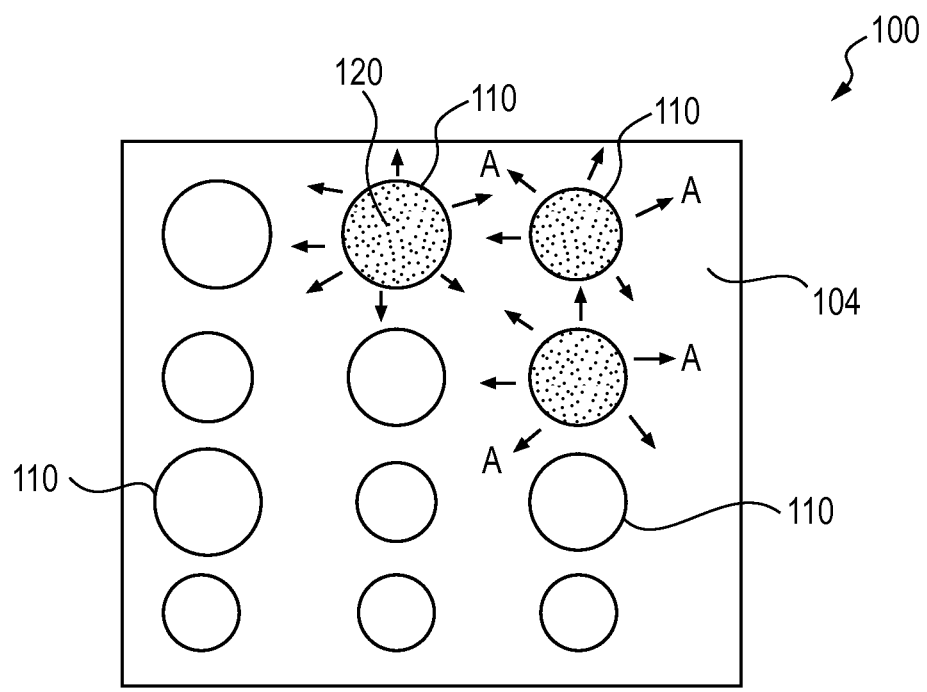
FIG. 4 is another view of the layer illustrated in FIG. 3 highlighting the efficient, controlled ingress of the agent into the adhesive and more particularly to the bonding interface.

Referring to FIG. 4, a top face 104 of the interior layer 100 from FIG. 3 is shown. Regions of adherend 120, such as skin, are exposed and thus accessible by the fluid through the wells 110. Since the bottom of the wells 110 represent the adherend, for example skin, fluids such as an adhesive deactivating agent, are then afforded an opportunity to quickly diffuse or otherwise transport through the interface to help weaken the adhesive bond and aid in easy, atraumatic debonding as shown in FIG. 4. Specifically, referring to FIG. 4, as fluid such as the adhesive deactivating agent travels through the wells 110 and directly contacts the adherend skin 120 as well as the layer of adhesive, the fluid then migrates radially outward from the periphery of each well 110, in the direction of arrows A. This configuration for wells 110 significantly promotes contact between the fluid and the adhesive and the interface.

A test method that can potentially probe this rate of interfacial diffusion is by the use of single frequency capacitance measurements (SFCM) using a spaced array of interdigitated electrode sensor plates. This is described in greater detail in the Test Methods section herein.

Figure 5:
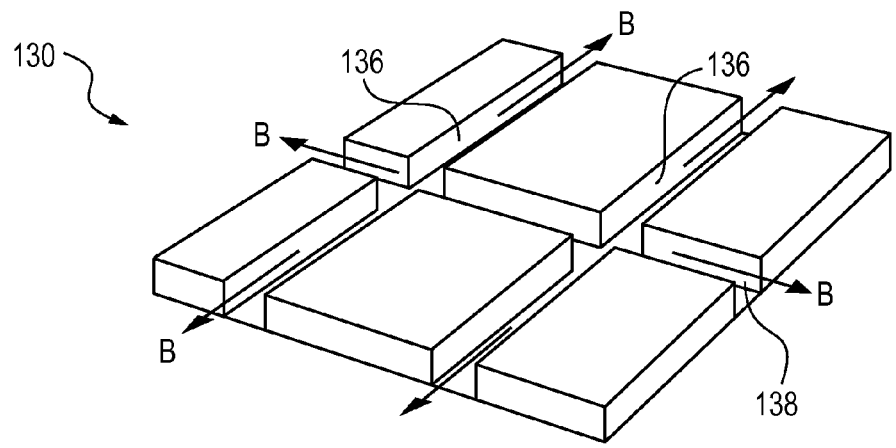
FIG. 5 is a schematic illustration of another preferred configuration for an adhesive layer utilized in a multilayer laminate in accordance with the present invention.

In yet another preferred embodiment in accordance with the present invention, a co-continuous void channel is provided within the layer of adhesive that allows for efficient distribution of fluid as shown in FIG. 5. One method for achieving such channels within an adhesive or backing layer is by mechanical embossing. Specifically, FIG. 5 illustrates a layer 130 of adhesive that is formed with one or more channels such as channels 136 and 138 that preferably extend at least partially across the layer 130 and generally within the plane of that layer. FIG. 5 illustrates a configuration in which the collection of channels includes a first set of generally parallel channels 136 and one or more transversely extending channels 138. Upon entry of fluid, such as an adhesive deactivating agent, into one or more of the channels 136 and 138, the fluid can rapidly be distributed throughout the adhesive layer as it flows in the direction of arrows B. This configuration may be useful if perimeter sealing around a wound is not particularly critical since egress of exudates through such channels may not always be acceptable. An effective method for quantifying the extent of air leak through the peri-wound area is available by utilizing a modified Sheffield Smoothness or the Air Permeability test. This is described in the Test Methods section herein.

Alternatively, such conduits or channels need not necessarily be in the form of voids but instead can be based upon selective phases that afford select or desired properties such as absorbing or dispensing adhesive deactivating agents, and may additionally include soft silicone gels for enhancing painless debonding, medicant releasing, etc.

Figure 6:
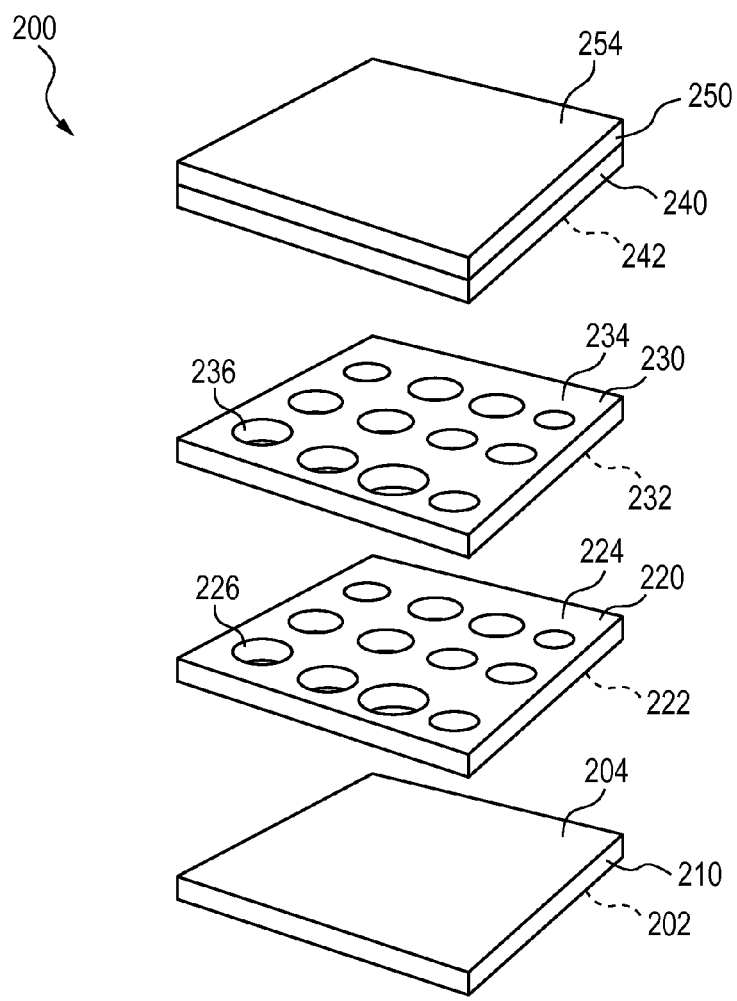
FIG. 6 is an exploded schematic illustration of another preferred embodiment multilayer laminate in accordance with the present invention.

In yet another preferred embodiment, a multilayer laminate similar to a "transfer tape" type product offering is depicted in FIG. 6. Specifically, a laminate 200 is provided comprising a release liner 210 defining a first face 202 and a second oppositely directed face 204. The laminate 200 also comprises an adhesive layer 220 with first and second faces 222 and 224, respectively, and defining one or more apertures 226. The laminate 200 further comprises an interior layer 230 defining first and second faces 232 and 234, respectively, and defining one or more apertures 236. The laminate also comprises a cover layer 250 carrying a layer 240 of a pressure sensitive adhesive, the layer 240 defining a face 242 for contact with the face 234 of the interior layer 230. The cover layer 250 defines an outer face 254, generally opposite the face along which is disposed the adhesive layer 240. The face of the cover layer 250 contacting the adhesive 240 is preferably configured relative to the face 234 of the interior layer 230 such that upon removing the cover layer 250, the adhesive layer 240 remains or is carried with the cover layer 250 as opposed to remaining on the interior layer 230. Although the invention is not limited to any particular amount of adhesive for layer 240, a typical amount is about 10 g/m². Choice of the adhesive may be the same as the one to use for skin contact or some other removal/low adhesion PSA like Air Products Airflex 920 or 7200. The interior layer 230 preferably defines a plurality of apertures 236, each having a diameter or span of from about 0.5 to about 10 mil. The adhesive layer 220 preferably defines a plurality of apertures 226 having an arrangement that is identical to or at least substantially similar as the arrangement of apertures 236 of the interior layer 230. And, the size of each aperture 226 in the adhesive layer 220 preferably is the same as that of a corresponding aperture 236 defined in the interior layer 230. Again, although the present invention is not limited to any particular amount of adhesive for layer 220, a typical amount is about 60 g/m². This embodiment has the advantage of being used as a universally usable double coated "transfer tape" with nearly any type of "top" film/PSA laminate. Accordingly, the present invention can be readily deployed in a wide array of products, systems, and applications.

In yet another embodiment of the present invention, the interior layer can be microporous, nonporous if optical clarity is important, and comprise a breathable fabric that allows fluids to readily pass through to an adhesive layer which is preferably channeled as shown in FIG. 5.

Another embodiment in accordance with the present invention is based upon the pressure sensitive adhesive having an open cell foam structure or being composed of microfibers or any other three dimensional architecture that allows for free fluid movement.

In yet another embodiment in accordance with the present invention, the channels in the adhesive layer such as shown in FIG. 5, are formed by using suspension-based pressure sensitive adhesive compositions.

The architecture and dimensions of the channels or passageways are selected in order to achieve a good balance between efficient delivery of the adhesive deactivating agent without unduly compromising initial peel adhesion to ensure secure attachment to the adherend.

Example 2

Figure 7:
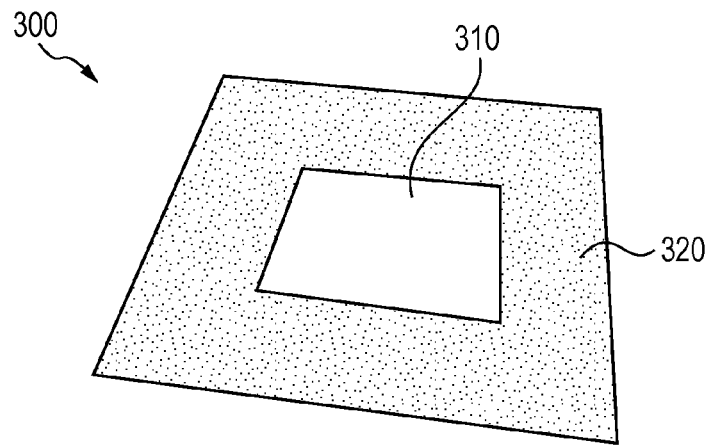
FIG. 7 is a schematic view of another preferred embodiment laminate in accordance with the present invention.

Vacuum assisted closure (VAC) drape dressings typically need to be optically clear and conformable with ability to hold negative pressures. FIG. 7 depicts another preferred embodiment that can afford "ouchless" debonding on demand. Specifically, the embodiment 300 comprises a central region 310 for placement over a wound and a vacuum air seal overlaminate. The outer region 320 of the embodiment 300 may correspond to the preferred embodiment laminates described herein. The drape dressing comprises the previously noted I-1827A production laminate available from the present assignee that is appropriately perforated for promoting initial adhesion and selective debonding performance. Once this perforated laminate is applied over the foam clad wound area resulting from treatment in accordance with VAC techniques, another nonpervious overlaminate is applied on top to ensure that the area is sealed to adequately maintain the required negative pressure therapy, optimum moisture vapor transmission rate (MVTR), optical characteristics, etc. Selective adhesive debonding is accomplished by applying one or more appropriate adhesive deactivating agent(s) to the peri-wound area just prior to removal of the laminate.

Figure 8:
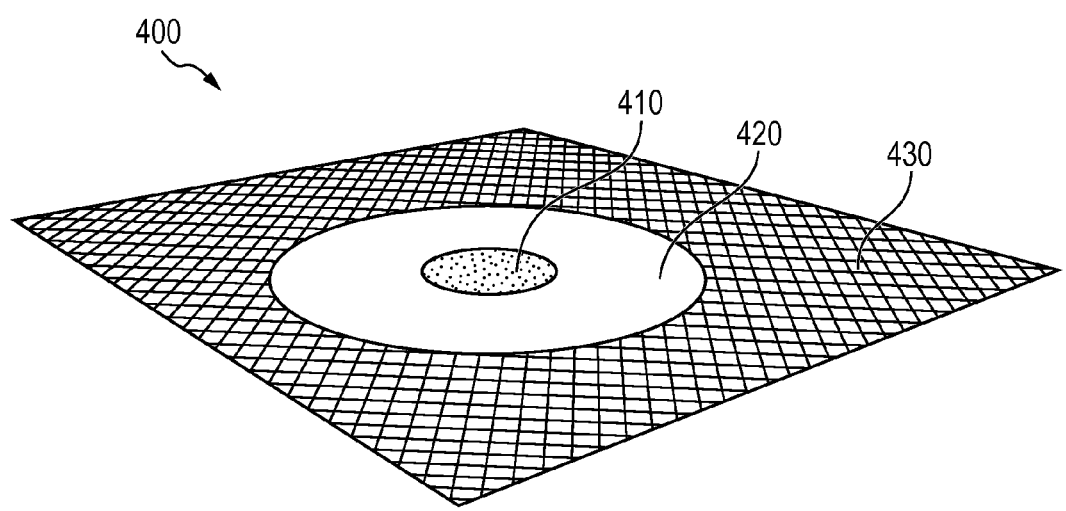
FIG. 8 is a schematic view of another preferred embodiment laminate in accordance with the present invention.

In still another preferred embodiment in accordance with the present invention, a laminate 400 which is selectively perforated in the peri-wound area is provided with a center region providing a secure seal as shown in FIG. 8. The center circular shaped region 410 is positioned over the wound area, and comprises VAC-suitable foam. This region is free of adhesive. The outer annular ring 420 area may also extend over the wound area, and so is free of adhesive. This annular area 420 may be optically transparent and nonpervious to retain the vacuum and/or fluids. The outer remaining region 430 utilizes the preferred embodiment laminate configuration described herein. While this embodiment is easier to use, it requires various pre-determined sizes to be fabricated rather than allowing the practitioner to cut the drape to size as needed. In this regard, see for example U.S. Pat. No. 4,917,112.

Yet another preferred embodiment in accordance with the present invention involves covering the wound with foam as is currently done in vacuum assist closure (VAC) therapy. One then further covers the foam with the minimum size of a low adhesion thin film laminate with non-pervious layers. The low adhesion is just enough to securely construct a "tent" around the wound area and lightly seal on the peri-wound skin. One can then drape a selectively debondable pervious laminate to complete the dressing and proceed to apply negative pressure to initiate the vacuum assist closure (VAC) therapy.

Yet another embodiment in accordance with the present invention is to use a variable combination of patterning adhesives and film to impart various desired properties such adhesion control, selectively debondable adhesion, air seal, etc.

Figure 9:
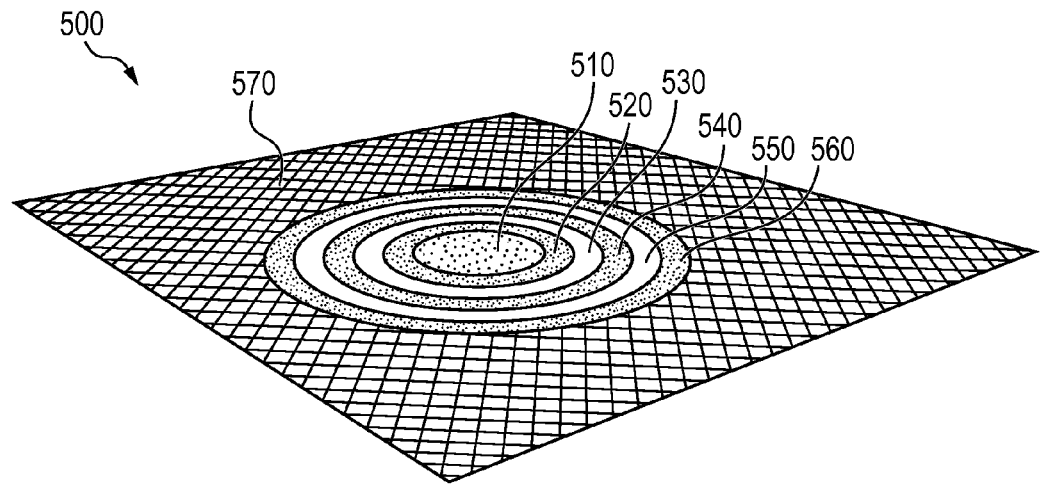
FIG. 9 is a schematic view of yet another preferred embodiment laminate in accordance with the present invention.

The laminate 500 depicted in FIG. 9 provides one possible way of achieving this. The centrally disposed circular region 510 is placed over the wound area. The collection of annular rings 510, 520, 530, 540, 550, and 560, are sized and patterned for air sealing and reduced adhesion as desired. The remaining outer region 570 utilizes the preferred laminate configuration described herein. It will be appreciated by one skilled in the art, that many combinations of patterns, adhesion levels, overlaminate film structure, etc. can all be mixed and matched to afford a combination of performance desired by the end user.

Figure 10:
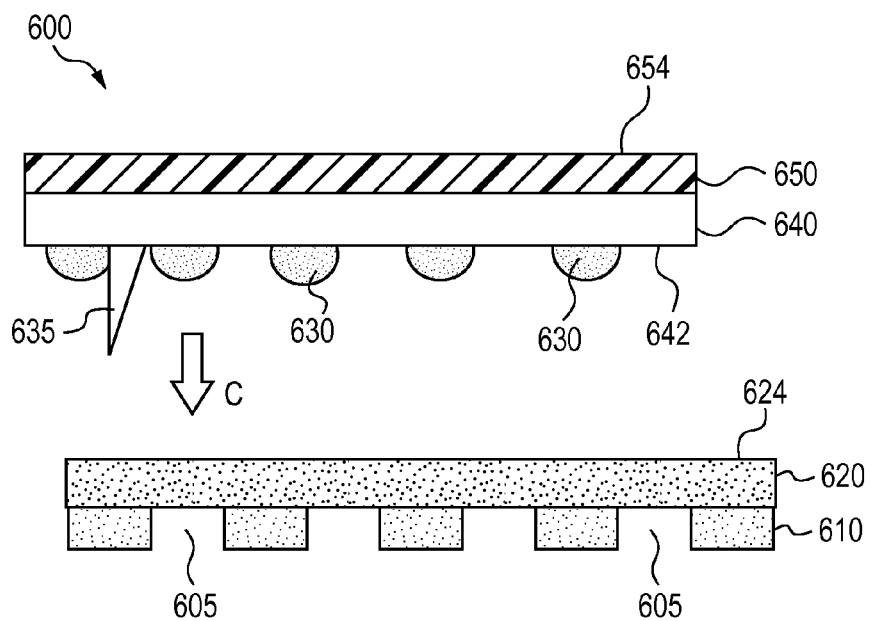
FIG. 10 is a schematic view of another preferred embodiment multilayer laminate in accordance with the present invention.

The present invention also provides an alternative delivery system as follows. This delivery system involves the use of delivering appropriately encapsulated agents in conjunction with microneedles configured and sized to perforate the interior layer and adhesive, on demand, when needed. This is depicted in FIG. 10. Generally, an interior layer 620 that is adhesively adhered to an underlying substrate by an adhesive layer 610, receives adhesive deactivating agent as described herein. The agent is contained within microcapsules 630 that are ruptured or otherwise configured to release the agent onto a face 624 of the layer 620. The microcapsules 630 can be carried by or otherwise incorporated within a layer 640 and/or the laminate 600. The microcapsules 630 can be attached to a face 642 of the layer 640. One or more optional microneedle (s) 635 can be provided to puncture the interior layer 620 to further promote delivery of the adhesive deactivating agent in the direction of arrow C to the adhesive. An optional cover layer 650 defining an outer surface 654 can also be provided. FIG. 10 illustrates the adhesive layer 610 defining one or more channels 605, as previously described with regard to FIG. 5.

This delivery system is particularly well suited for the application of such laminates over a previously applied adhesive bandage. When one wants to remove bandages already perforated as is typical of many commercial products, one simply post adheres one of these Atraumatic Adhesive Removal (AAR) laminates which have been previously engineered to align the adhesive patch sections to carrier sections containing adhesive-removal aid. Such laminates will have pre-patterned adhesive layers to help attach to the old skin adhered bandage for a prescribed length of time to allow for effective fluid ingress needed for pain-free removal. The optional microneedles shown are positioned to coincide with the location of the adhesive areas of the bandage when a previously perforated top film is not available e.g. occlusion laminates.

Example 3

Another embodiment of the invention that extends this concept, additionally utilizes a peri-wound covering that is attached to an area surrounding a wound. This provides the surface to which products such as a vacuum assist closure (VAC) therapy film are adhered. Since the adhesive in these products does not directly contact the skin, one can further minimize the pain, allergy, etc. that is inflicted by their repeated use of bonding and debonding from the upper surface of the pen-wound covering. The pen-wound pseudo-skin shield can be designed to stay securely attached to the skin for times significantly longer than typical medical dressings. Since the present invention can be used for eventual atraumatic removal, this may offer significant advantages to the nurse or patient.

Figure 11:
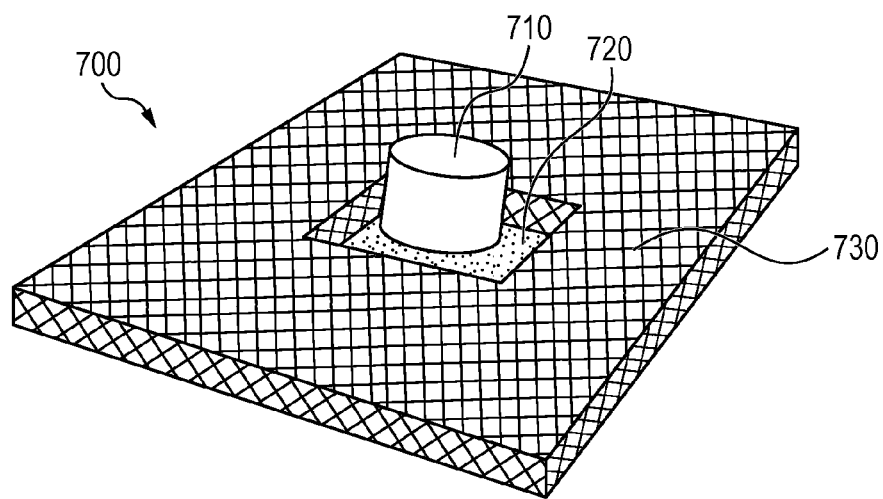
FIG. 11 is a schematic view of yet another preferred embodiment laminate in accordance with the present invention.

The material used in such pseudo-periskin shields can alternatively be designed to be selectively destructed, on demand, using selective adhesive debonding strategies. Referring to FIG. 11 for example, a laminate 700 is provided defining a central region 720, preferably recessed, and an outer region 730. The central area 720 is placed over the wound area and comprises a foam material 710 suitable for use with vacuum assist closure (VAC) therapies. The remaining regions 730 can utilize a laminate construction as described herein and which affords repeated atraumatic use. Preferably, the upper surface of the region 730 can be engineered to minimize the pain and discomfort associated with repeated bonding and debonding of VAC products which may be adhered thereto.

Figure 12:
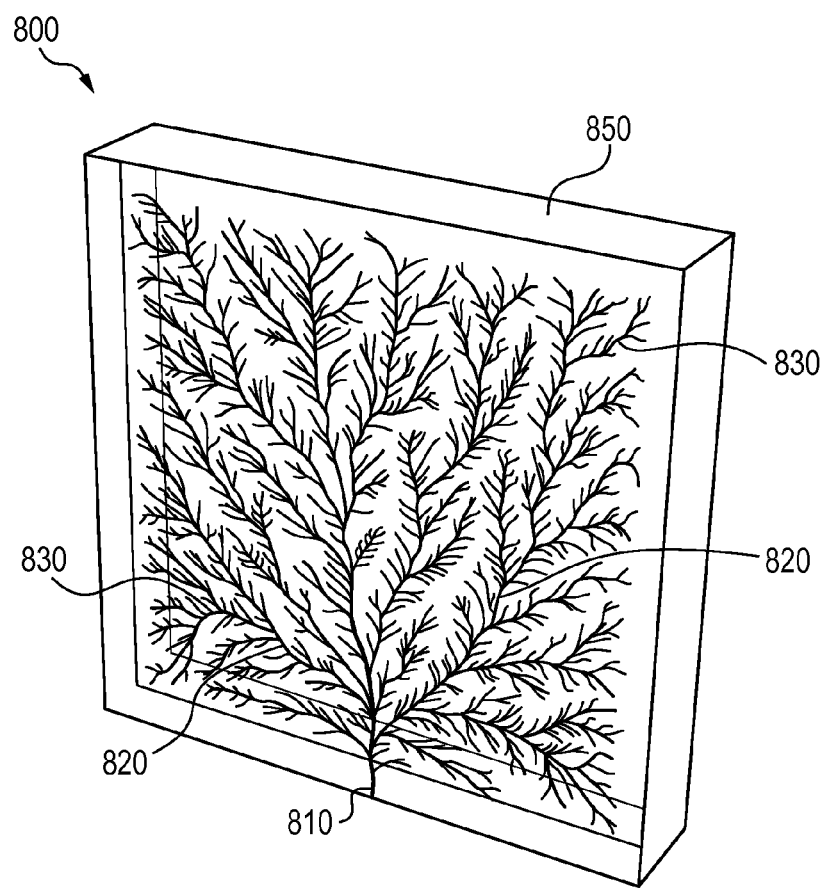
FIG. 12 is a schematic representation of an aspect of the present invention.

Another embodiment of the present invention utilizes a fractal-based channel system so fluids can be readily delivered throughout a medium from a single or very few injection entry points. An example of a fractal pattern is represented by a Lichtenberg figure as shown in FIG. 12. As known by those skilled in the relevant arts, Lichtenberg figures are branching tree-like or fern-like patterns that tend to appear similar at various scales of magnification. This characteristic, often referred to as "self-similarity" is a key property of fractals. Referring to FIG. 12, a primary branch 810 includes a plurality of secondary branches 820. Each secondary branch 820 comprises a plurality of tertiary branches 830, and so on. The branches may constitute voids or channels defined in a layer 850. For example, the previously described channels defined in the adhesive layer could be configured in accordance with a fractal pattern. It is also contemplated that the apertures formed within the interior layer of the preferred embodiment laminates could also be arranged in such a pattern.

The present invention also contemplates another technique for delivering a debonding fluid, i.e. an adhesive deactivating agent. In this version of the invention, one or more agents are administered in a gas or air, and then introduced by pumping the gas or air using the vacuum assist closure (VAC) therapy device or some other means.

The present invention contemplates the possibility of applying a low level of heat above ambient temperature to the laminate in order to adhere the laminate to a surface or to cause shrinkage of the film or a combination of both. In addition, chemical treatments can be used to cause shrinkage of the film and to adhere the film to the surface.

Any of these structures and/or techniques may be incorporated in a preferred embodiment laminate to provide selective adhesive debonding or a peri-wound pseudo skin covering for fluid activation.

Additional Applications Involving Ease of Handling

Figure 13:
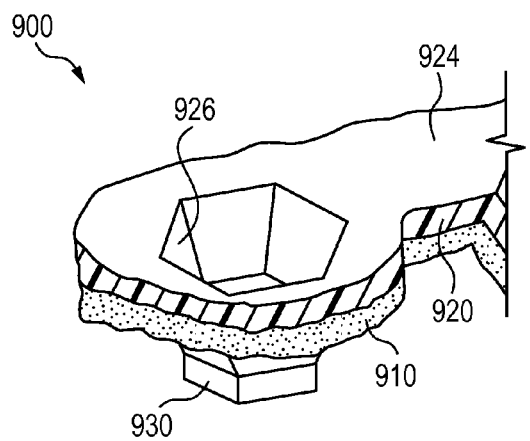
FIG. 13 is a schematic view of another aspect of the present invention.

Since many medical applications call for the use of highly conformable, optically transparent adhesive dressings, the present invention further extends the utility of U.S. Pat. No. 6,541,098 owned by the present assignee. Specifically, the "tack on" adhesive function described in that patent can be utilized in the preferred embodiment laminates described herein. Referring to FIG. 13, a laminate 900 is provided having one or more layers 920 and a recessed layer 910 of a pressure sensitive adhesive. One or more apertures 926 are formed through the layer(s) 920 such that material from those layers extends beyond the exposed face of the adhesive layer 910. The resulting material projections 930 serve as "standoffs" or protuberances which preclude or at least limit the degree to which the adhesive layer 910 can be contacted with a substrate. Upon application of a compressive force to a face 924 of the laminate 900, the adhesive layer 910 can then be contacted with a substrate, thereby enabling the laminate 900 to be adhesively adhered to the substrate. The details relating to these aspects are set forth in the previously noted U.S. Pat. No. 6,541,098. In accordance with the present invention, the laminate 900 containing stand-offs with adhesive, also comprises an apertured interior layer designed for transport and passage of an adhesive deactivating agent.

The present invention also readily provides for a thin, transparent, conformable laminate that provides an advantage of being linerless due to engineered embossing. Such a construction utilizing an appropriate medically acceptable adhesive helps overcome a common handling problem when the articles stick to themselves. In accordance with the invention, the surface is rendered non-tacky until an appropriate amount of pressure is applied. It is important to recognize that the adhesive is present continuously thereby providing good sealing around the wound needed for vacuum assist closure (VAC) therapies.

Figure 14:
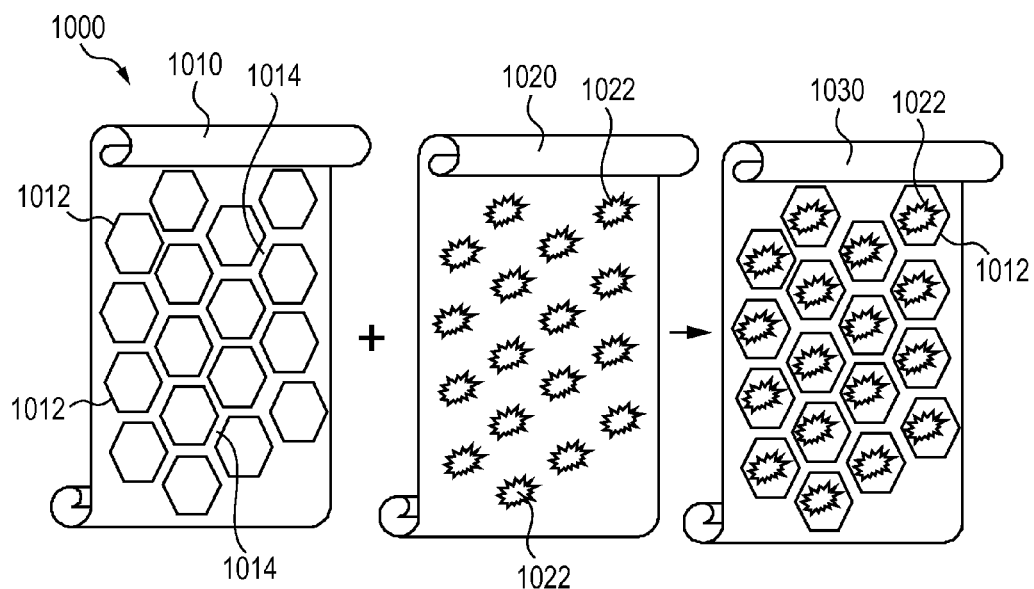
FIG. 14 is a schematic illustration of another aspect of the present invention.

In yet another aspect of the invention, one can extend this feature to a laminate to additionally provide easy peel-off characteristics. FIG. 14 illustrates an example of one such embodiment 1000. In this version of the present invention, a plurality of spaced "hills" or projections 1012 along a face of layer 1010 are formed. The non-projecting regions 1014 between the hills contains pressure sensitive adhesive. A perforated layer 1020 defining a collection of apertures 1022 is provided and positioned such that the apertures 1022 are aligned with the projections 1012. Preferably, each aperture 1022 is centered with respect to a corresponding projection 1012. A resulting laminate 1030 can be formed. It will be understood that the present invention includes a wide array of varied and derivative laminate structures employing this configuration.

The choice of adhesive chemistry, coat weight, printed percentage coverage, and other factors, are preferably tailored to provide for adequate adhesion, air sealing, moisture vapor transmission rate (MVTR), wet-stick properties, and the like. Other embodiments are contemplated that reflect this approach.

Other approaches that potentially afford ease of handling adhesive articles, especially when they are thin, include the following strategies.

Figure 15:
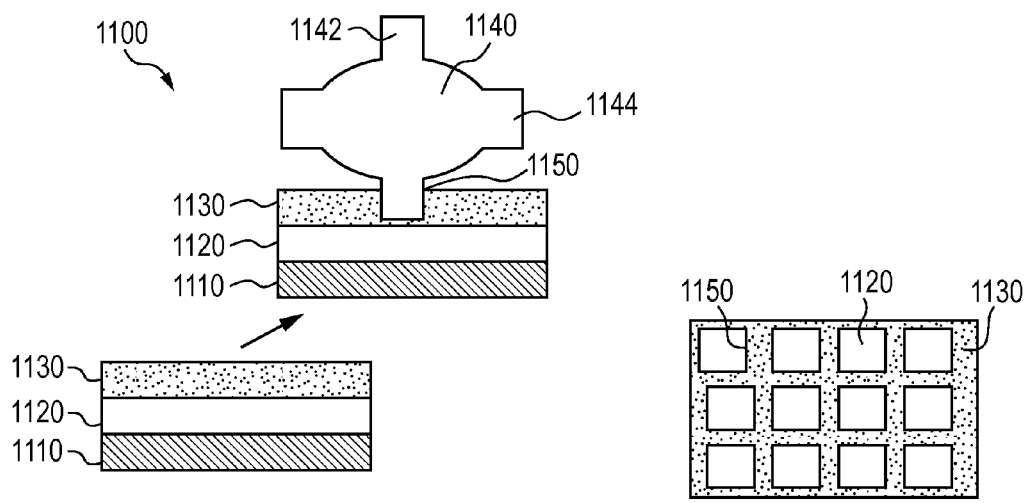
FIG. 15 is a schematic illustration of a technique promoting ease of handling and resulting laminate in accordance with the present invention.

Overlaying a perforated film, as shown by the technique 1100 in FIG. 15 can be utilized. In this approach, a layer of a pressure sensitive adhesive 1120 is disposed between a conformable face film 1110 such as formed from polyethylene or polypropylene, and a perforated film 1130. Upon removal of one or more perforated regions from the perforated film, the adhesive is exposed through apertures 1150. An embossing die 1140 having one or more projections or tips 1142, 1144 can be used to form the apertures 1150. This layered configuration can be utilized in conjunction with a selectively apertured layer providing for transport of an adhesive deactivating agent. This approach can be used to significantly improve ease of handling of the adhesive carrying laminates described herein.

Figure 16:
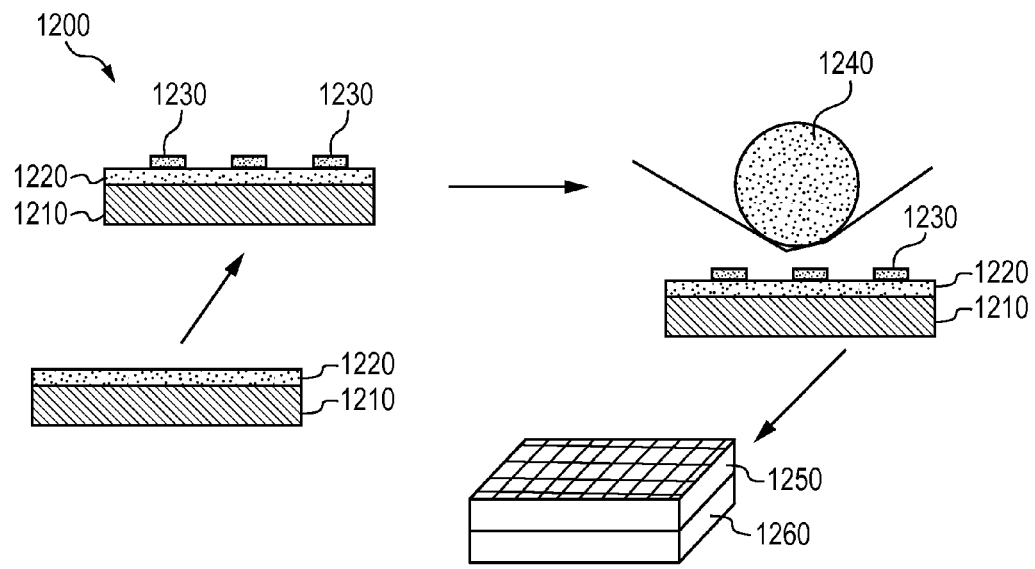
FIG. 16 is a schematic illustration of another technique and resulting laminate in accordance with the invention.

The use of liner preprinting with non-tacky, transferable moieties, as shown in the technique 1200 in FIG. 16 can be utilized. In this approach, printing or other suitable material deposition operation is performed to deposit a material 1230 such as ink upon a face of a release coating 1220 carried on a liner 1210. The deposited material 1230 on the liner 1210 is then contacted with an adhesive layer 1250 and film 1260 or, as in the present invention, a laminate carrying a pressure sensitive adhesive as described herein. A transfer component 1240 can be used. The transfer of the material 1230 onto the adhesive layer 1250 can significantly improve ease of handling of the adhesive carrying laminate.

A prime application of this strategy is in the formation and production of printed ink conduits that serve to deliver one or more adhesive deactivating agents to a targeted location, i.e. such that the agent(s) can efficiently disrupt the substrate-adhesive bond or bonding interface. Preferably, the printed ink conduits are deposited upon a release coating carried on a liner as depicted in FIG. 16. For certain applications, the use of liner printed ink conduits provides a commercially viable approach by which to rapidly deliver the adhesive deactivating fluid so that it can disrupt the substrate-adhesive bond or interface.

Although the various strategies described herein for forming printed ink conduits are not limited to any particular ink formulation, the following are representative examples of preferred inks. For instance, the ink available under the designation UV Cured Gravure Ink, No. 982-64 from DAW Ink, has been identified as suitable for these strategies. Additional details and aspects of the methods and approaches in accordance with FIG. 16 are provided in U.S. Pat. Nos. 7,332,205; 7,344,618; and 6,630,049.

The ink is formulated so that it can be readily printed on a low energy surface such as on a silicone release material, and also able to withstand subsequent process abuse such as exposure to wet solvents, other coatings, heat, pressures and other factors.

These strategies as generally described herein and particularly in conjunction with FIG. 16 enable the formation of an appropriately printed liner or other component that can be universally used to transfer the ink conduit pattern to any adhesive surface. The transfer technique can be any appropriate method such as by wet coating or by a delamination-relamination process. Furthermore, these strategies enable the area of printed ink coverage to be used to tailor peel adhesion characteristics by controlling the contact area. Thus, these strategies provide yet another approach for concomitantly mitigating pain during debonding. These strategies also enable the chosen print pattern to control fluid ingress or egress properties. For example, a print pattern of continuous traces readily assists in transporting fluid ingress from a laminate edge or other region, to spread efficiently through the trace pattern. In contrast, a discontinuous ink pattern presents a contiguous adhesive contacting surface that may be needed when attempting to retain a negative pressure such as in a NPWT/VAC therapy system.

Example 4

A series of investigations were conducted as to the effect of different surface printed ink patterns on peel adhesion of a multilayer laminate including a medical grade acrylic pressure sensitive adhesive.

Two categories of samples were prepared, schematically depicted in FIG. 26. Each sample included an exposed face having printed regions of ink conduits and adhesive regions. FIGS. 26A and 26B illustrate sample faces having adhesive regions "a" and printed ink regions "b". Sample A has a print region b that occupies 66% of the total area. Sample B has a print region b that occupies the same proportion of surface area, i.e. 66%. However, it will be appreciated that the pattern of the printed regions b in Sample A is discontinuous, while that of Sample B is continuous. Preferably, the printed ink conduit patterns define a plurality of continuous flow channels, or if desired, a plurality of discontinuous flow channels.

The samples were then subjected to ninety degree peel adhesion tests against control samples, i.e. the corresponding laminate having a 100% adhesive coverage face, and the corresponding laminate having 20% of its surface area perforated. Samples were tested after varying dwell time periods using an Instron® device obtaining peel adhesion measurements at 12 inches per minute. Table 2 set forth below summarizes the results of this investigation. Another set of trials were also conducted in which the evaluations were performed using polyurethane (PU) based skin models.

TABLE 2

Comparison of Peel Adhesion Values

| Sample ID | 90 Degree Peel Adhesion on skin after 2.5 hr dwell (lbs/inch) | 90 Degree Peel Adhesion on skin after 24 hr dwell (lbs/inch) | 90 Degree Peel Adhesion on PU based skin model after 20 min dwell (lbs/inch) |
|---|---|---|---|
| Control | 3.5 | 4.5 | 7.5 |
| Control with 20% area perforated | 1.9 | 4.3 | 6.4 |
| Sample B | 0.6 | 2.8 | 5.9 |
| Sample A | 0.4 | 2.7 | 6.4 |

As evident in the data presented in Table 2, the Samples A and B exhibited significantly reduced peel adhesion values compared to the control and the control having 20% of its face area perforated.

Example 5

FIG. 27 illustrates printed ink conduits as described herein and designated as "RS" in FIG. 27. The printed ink conduits promoted fluid ingress and fluid retention as compared to a control. Specifically, FIG. 27 gravimetrically depicts how a volatile fluid such as HMDS (hexamethyldisiloxane) rapidly enters and continues to remain within an adhered laminate over time.

Example 6

Another series of investigations were conducted in which 90 degree peel tests were performed upon samples using high density polyethylene (HDPE), and varying coat weight with a 20 minute dwell time.

Figure 28:
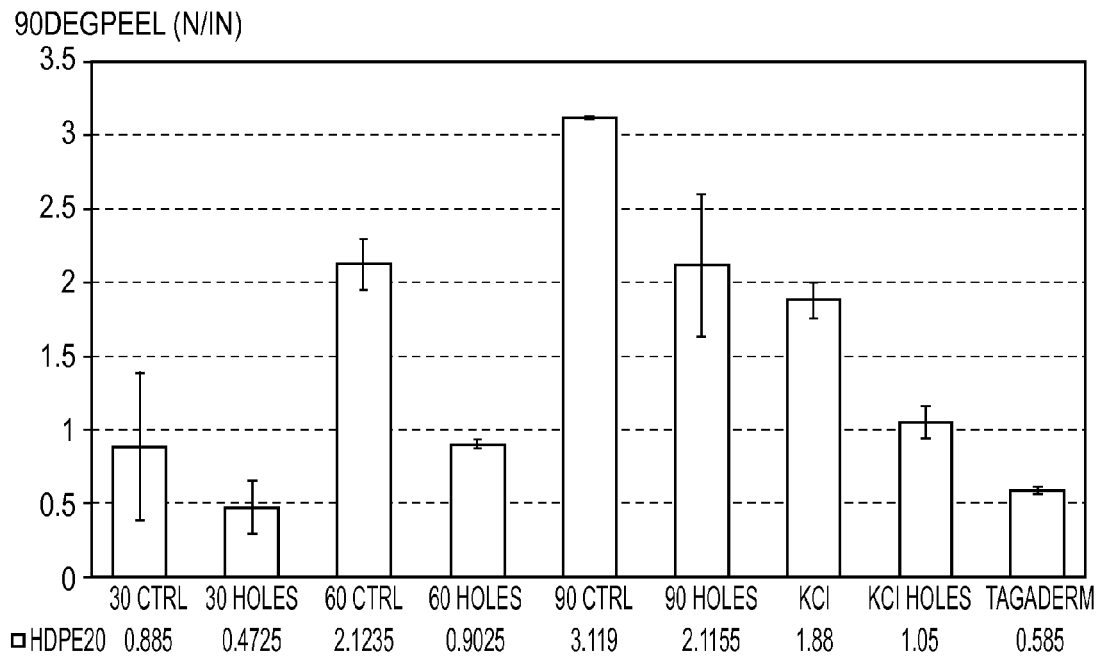
FIG. 28 is a graph of peel strength values of various samples.

FIG. 28 illustrates various samples as noted along the horizontal axis of the graph and the corresponding 90 degree peel measurement. Interestingly, a 20% perforated 90 gsm coat weight affords a 20 minute dwell peel adhesion comparable to a currently commercially available non-perforated product coated at 60 gsm. A reduction in the peel adhesion after a longer dwell time period, i.e. longer than 24 hours, is much less and is more proportional to the percentage of area lost from perforation. Regardless of the initial high peel adhesion, use of a preferred adhesive deactivating agent or like fluid immediately reduces the HDPE peel adhesion to less than 0.3 N/inch. This is significant and remarkable.

Although not wishing to be bound to any particular theory or parameters, it is believed that in order to obtain a rapid debond on demand response, such as within approximately 10 to 20 seconds, providing a flow area that is approximately 20% of debond on demand channels is preferred. Investigations indicate that 10% of debond on demand channels is too low, and 40% may be extragent thereby rendering the laminate structurally flimsy however providing an impressive response. A successful negative pressure wound therapy (NPWT) drape with debond on demand attributes using an overlaminate, was produced.

In an alternate embodiment, a NPWT assembly drapes a sponge-containing wound bed with a fully perforated laminate. Using a "cut-to-size" T.R.A.C. pad modification, a center wound bed area can be covered with a non-perforated laminate film. By covering the underlying perforation(s), this promotes secure negative pressure in the wound bed and also eliminates a need for creating a puncture or other access for a vacuum tube as is currently practiced.

Figure 29:
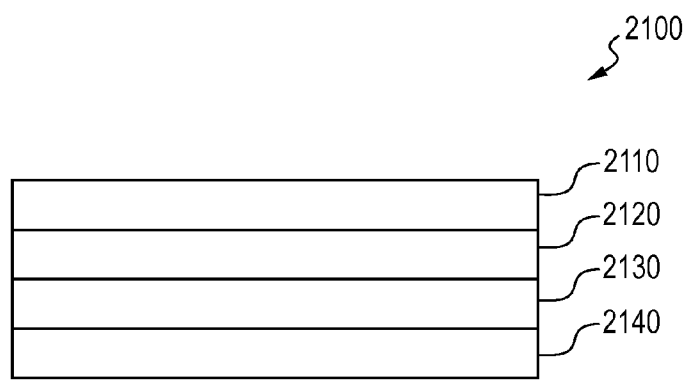
FIG. 29 is a schematic illustration of another preferred embodiment laminate.

FIG. 29 illustrates another preferred embodiment multi-layer laminate or assembly 2100 as follows. The assembly 2100 comprises a film layer 2110, an adhesive layer 2120, a controlled infraction layer 2130, and a substrate 2140. The controlled infraction layer 2130 serves to selectively disrupt and/or dissolve upon exposure to an adhesive deactivating agent. This layer, such as layer 2130, has several preferred characteristics such as (i) not compromising the adhesion between the adhesive and substrate, i.e. layers 2120 and 2140, but also (ii) is readily disputable and/or dissolvable using an appropriate configured composition or adhesive deactivating agent or like fluid. The infraction layer can be used instead of or in conjunction with the previously described multilayer laminates having a plurality of fluid passageway conduits or apertures such as in an interior layer exhibiting a controllable flow profile.

The controlled infraction layer can be readily delivered in the form of a spray, wet wipe, etc. The controlled infraction layer can be used in conjunction with printed ink conduits as described herein. In certain preferred embodiments and applications, the infraction layer is sacrificial and so may degrade and/or be progressively removed or otherwise eliminated such as during removal of the various multilayer laminates described herein.

The controlled infraction layer can also comprise a wide array of other agents and/or components. For example, the controlled infraction layer may also comprise medicants such as pain relief agents, anti-allergy agents, etc.

The controlled infraction layer can additionally exhibit unique functional electrical features for enabling improved diagnostics, such as for example relating to dielectric constants, conductivity, etc. An example of such layer may be in components for providing or interfacing with wireless vitals monitoring patches. The infraction layer could be configured to provide a reliable interface for signal reception by the patch.

The infraction layer can also be configured to provide a switchable functionality. In this embodiment for example, a temperature sensitive side chain crystalline polymer could be incorporated in the layer to provide selective permeability to actives depending upon the activation stimuli, for example heat. Generally, the infraction layer can have a switchable functionality whereby a physical property of the layer changes between at least two states as a result of a change in external stimuli.

In yet another embodiment, an assembly is provided that is particularly directed to mitigating pain associated with repeated peeling off from the same area. In this version, a strongly adhered "moat" serving as an interface layer is provided around the pen-wound area. These assemblies can be configured and designed to robustly provide robust sealing, and be used for repeated bonding and debonding without disrupting the user's skin. And, using an appropriate methodology, this layer can be replenished as desired. Such an attachment interface system can be used in a wide range of medical applications besides NPWT. An example of such a medical application is ostomy care. The interface may be laid down or otherwise applied either via a spray or wet wipe application, or may be positioned and/or applied using an appropriately designed attachment aiding device.

Figure 17:
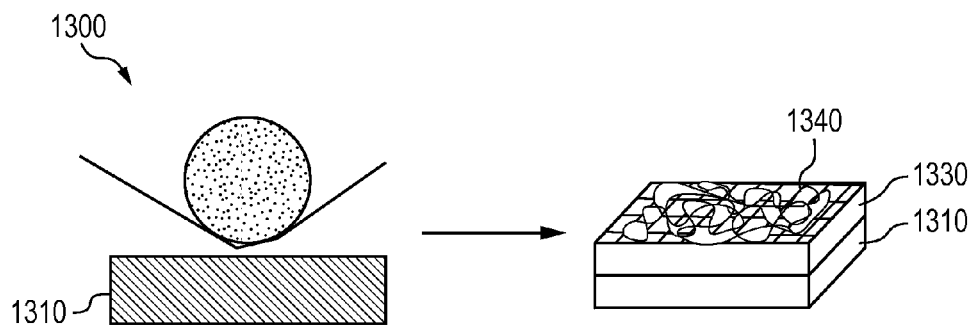
FIG. 17 is a schematic illustration of another technique and resulting laminate in accordance with the invention.

Overlaying non-wovens, as shown in FIG. 17 can be used. In this approach designated as 1300, a thin layer of a non-woven material 1340 is deposited onto the adhesive face 1330 of an adhesive carried by a film 1310. The non-woven layer 1340 on the adhesive significantly improves ease of handling of the laminate.

Figure 18:
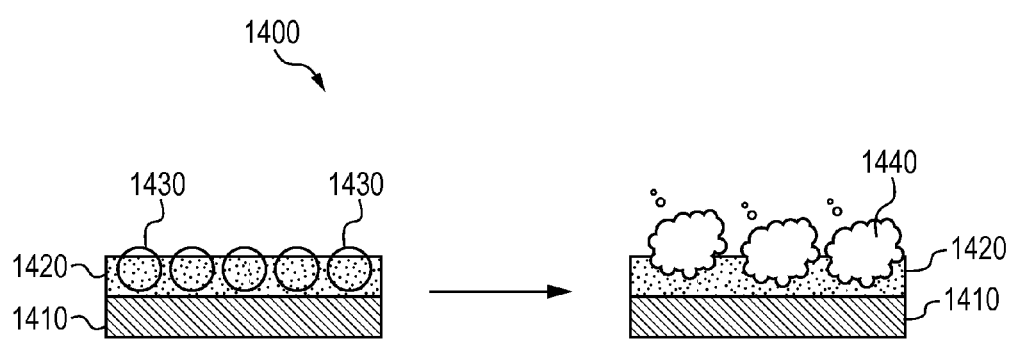
FIG. 18 is a schematic illustration of another technique and resulting laminate in accordance with the invention.

Dusting the adhesive surface with Expancel beads (expanded or unexpanded) from Akzo Nobel, elastic microspheres, mica, ink, etc., as shown by technique 1400 in FIG. 18 can be utilized. In this approach, an effective amount of particulate matter 1430 is deposited onto an exposed adhesive face 1420 carried on a film 1410. As will be appreciated by those skilled in the art, the micropheres can be expanded or otherwise treated to leave or form a residue layer 1440. This practice can be used to improve ease of handling of the adhesive-carrying laminate.

Figure 19:
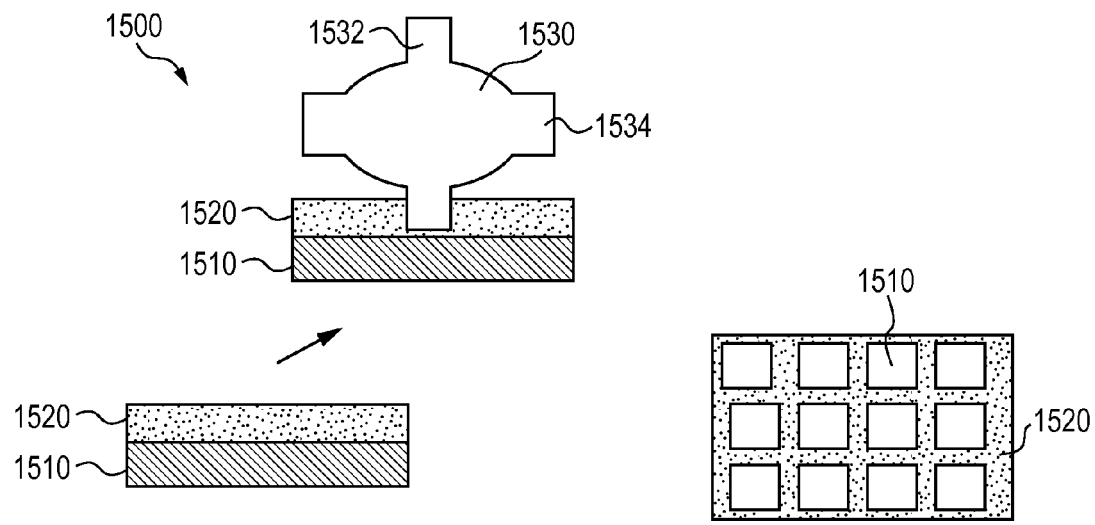
FIG. 19 is a schematic illustration of another technique and resulting laminate in accordance with the invention.

Overlay of a heat, light or fluid activatable adhesion allowing layer, as shown in FIG. 19 can also be used. In this approach designated as 1500, for example, a thermally activated pressure sensitive adhesive 1520 is applied onto a conformable face layer 1510 such as formed from polyethylene or polypropylene. Select region(s) of the adhesive are then heated, such as by contact with a hot tipped 1532, 1534 embossing roll 1530 to either deactivate, activate, or otherwise modify one or more properties or characteristics of the adhesive 1520. The heated or otherwise treated regions of the adhesive 1520 are shown as regions 1510. This strategy can be utilized in the various laminates described herein.

In addition, strategies for providing better film handling with a patterned modulus can be used.

Figure 20:
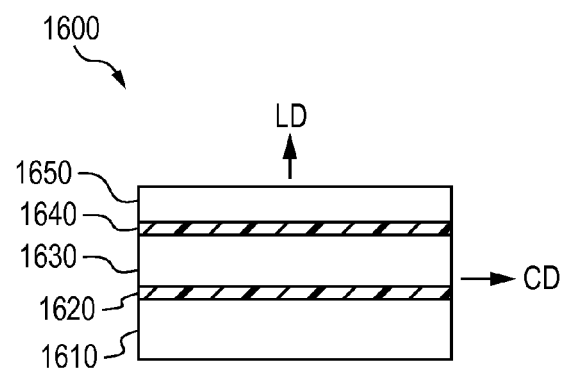
FIG. 20 is a schematic illustration of another preferred embodiment multilayer laminate in accordance with the invention.

Furthermore, Z-modulus polyvinyl chloride (PVC) films that are stiff in one direction and very compliant in the other as shown in FIG. 20 can be used. In this approach, a layered arrangement 1600 is prepared such that the laminate is relatively stiff in one direction and relatively compliant in another direction. The laminate 1600 comprises alternating layers of a polymeric material such as polyvinyl chloride with an effective amount of plasticizer, shown as layers 1610, 1630, and 1650; wherein each of the layers is separated by a layer of the polymer, and preferably the same polymer as used in layers 1610, 1630, and 1650 but without plasticizer. These layers are designed as layers 1620 and 1640. As shown by the data in Table 3 below, the laminate 1600 is significantly stiffer in the cross direction (CD) than in the length direction (LD).

TABLE 3

| Orientation | Young's Modulus (psi) | % Strain @ Break | Stress @ 8% Strain | Residual Stress (psi) |
|---|---|---|---|---|
| LD | 1,069 | 270 | 82 | 88 |
| CD | 8,416 | 271 | 482 | 213 |

Figure 21:
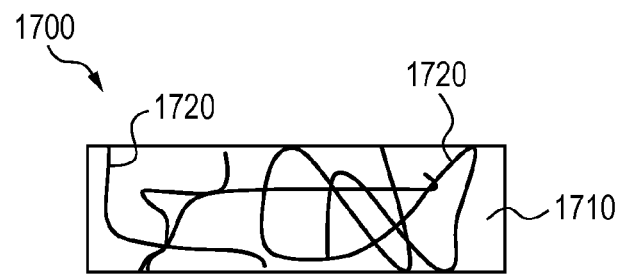
FIG. 21 is a schematic illustration of an aspect of the present invention.

Also, multiphase extruded film systems can be utilized in the present invention laminates. FIG. 21 illustrates a layer 1700 of a multiphase adhesive system including a matrix phase 1710 and a tacky phase 1720 typically dispersed therethrough. For example, a two phase system containing a tacky phase, such as available from Capitol Plastic Technology can be used.

Materials
Perforated Interior Layer

The interior layer of the preferred laminates such as for example layer 40 in FIG. 1, layer 100 in FIG. 3, and layer 230 in FIG. 6, can be formed from numerous materials. Preferred materials include but are not limited to elastomeric polyurethane, polyester, or polyether amide films. Desirable properties include high moisture vapor and oxygen permeability, resiliency, conformability and transparency. Disposable secondary backing films like polypropylene (PP) or polyethylene (PE) can be used to provide additional ease of handling. Alternatively, breathable paper or textile backings may also be appropriate for use. Additional examples of such paper or textile backings are provided in "A Review on Designing the Waterproof Breathable Fabrics," A. Mukhopadhyay; V. K. Midha, Journal of Industrial Textiles, Part 1-37, 225 (2008) & Part II—38, 17 (2008) and in U.S. Pat. No. 6,495,229 and related patents.

Cover Layer

A wide array of materials can be used for one or more cover or backing layer(s) such as layer 60 in FIG. 1 or layer 250 in FIG. 6, such as but not limited to, polyurethane, paper, polyethylene, polypropylene, and other polymeric film layers. Preferred aspects for each of these materials are as follows.

Polyurethane—Melt-blown non-woven fibrous webs comprised of three-layer polymeric fibers having a center layer of blended polyethylene and KRATON, pressure sensitive adhesive, and outer layers of polyurethane; prepared as described for Backing Sample 16 in U.S. Pat. No. 6,107,219 to Joseph et al.; represents a suitable elastic, non-tearable backing or cover layer.

Paper—Hammermill Laserprint paper (0.11 mm thick, Product No. 00460-4, International Paper, Memphis, Tenn.); represents a typically non-stretchable, tearable backing.

Polyethylene—Melt-blown non-woven polyethylene (0.04 mm thick, Style No. TM07-27-98-02, Trans Web LLC, Vineland, N.J.); represents a typically stretchable, tearable backing.

Polypropylene—Melt-blown non-woven polypropylene (basis weight 20 g/m$^2$, Kimberly Clark, Irving, Tex.); represents a typically non-stretchable, tearable backing.

Film—Polymer film comprising 60% ethylene/vinyl acetate copolymer, 35% linear low density polyethylene, 5% stabilizers and other additives (PGI Product No. 6012, Polymer Group, Inc., Gainesville, Ga.); film had a basis weight of 1.15 oz/yd$^2$ (27 g/m$^2$), was 5-mils (0.13 mm) thick, and had oval-shaped holes (approximately 0.2 mm width×0.3 mm length in the greatest dimensions) with the length dimension of the oval holes oriented parallel to the machine direction of the film. The film had about 530 holes/cm$^2$ arranged in a pattern of staggered lines. One side of the film was "smooth" (microetched/embossed for smoothness) and the other side was "rough" (side that had material pushed out from forming the holes).

Additional details of various materials suitable for cover layers are described in U.S. Pat. No. 7,078,582.

Adhesive

The adhesive used in the various preferred embodiment laminates such as in layers 30 and/or 50 in FIG. 1, layer 130 in FIG. 5, and layers 220 and/or 240 in FIG. 6, can be solvent, emulsion, suspension, 100% solids or hot melt in nature. Regulatory compliance may be required for medical application, for example in accordance with ISO 10993. The adhesive may be in the form of hydrogels, hydrocolloids, soft silicone gels, and may additionally incorporate "switchable" characteristics as previously discussed herein. Generally, it is preferred that the adhesive be a pressure sensitive adhesive.

The solvent-based acrylic adhesive may be any pressure sensitive adhesive that is capable of adhering to mammalian skin and that is free of ingredients known to cause undue irritation or toxicity to mammals. Useful acrylate copolymers may or may not be self-crosslinking and are formed from at least two monomers chosen from: (1) hydroxyalkyl esters of acrylic or methacrylic acid in which the alkyl group comprises 2 to 4 carbon atoms, such as 2-hydroxyethyl acrylate, 2-hydroxyethyl methacrylate, 2-hydroxypropyl acrylate and 2-hydroxypropyl methacrylate; (2) alkyl esters of acrylic or methacrylic acid in which the alkyl group of the ester comprises 4 to 18 carbon atoms, such as nbutyl acrylate or methacrylate, isopropyl acrylate or methacrylate, n-hexyl methacrylate and 2-ethylhexyl acrylate; (3) α,β-unsaturated monocarboxylic or dicarboxylic acids, their anhydrides and their alkyl or alkenyl esters in which the alkyl group contains from 1 to 3 carbon atoms and the alkenyl group contains from 2 to 5 carbon atoms, such as acrylic acid, itaconic acid, maleic acid, maleic anhydride, alkyl methacrylate and the diethyl esters of fumaric or maleic acid; (4) vinyl monomers, such as vinyl acetate, acrylonitrile, vinyl propionate, vinylpyrrolidone and styrene; (5) monomers containing a functional group selected from amido, amino and epoxy groups, for example, acrylamide, N-butylacrylamide, alkylaminoalkyl and aminoalky derivatives of acrylic or methacrylic acid, such as amino-ethyl acrylate, aminoethyl methacrylate and 2-(dimethylamino) ethyl methacrylate, glycidyl methacrylate and glycidyl acrylate; (6) alkoxyalkyl esters of acrylic or methacrylic acid, for example methoxyethyl acrylates or methacrylates, butoxyethyl acrylates or methacrylates, methoxypropylene glycol acrylates or methacrylates and methoxypolyethylene glycol acrylates or methacrylates; and (7) hexamethylene glycol dimethacrylate. As these copolymers can be self-crosslinking, they may also contain a crosslinking agent selected from those generally used by those skilled in the art, for example, organic peroxides, polyisocyanates, chelates or metals such as titanium or aluminum, or metal acetylacetonates, such as those of zinc, magnesium and aluminum.

These adhesive acrylate copolymers may take the form of solutions in a solvent system consisting of a single organic solvent or a mixture of several solvents, which contain about 25% to about 55% by weight copolymers. Examples of suitable solvents include aromatic solvents such as toluene, xylene, etc. Suitable aliphatic solvents include esters such as ethyl acetate, propyl acetate, isopropyl acetate, butyl acetate, etc.; ketones such as methyl ethyl ketone, acetone, etc.; aliphatic hydrocarbons such as heptanes, hexane, pentane, etc. There can be included in the adhesive composition additive materials that do not affect the basic properties of the adhesive. Fillers, tackifiers, antioxidants, stabilizers, and the like may be added to the formulate adhesive. Further, pharmaceutically active components, such as for example, antimicrobials, anti-inflammatory agents, analgesic agents, anesthetics, or other pharmaceutically acceptable compounds, which do not affect the basic properties of the adhesive can be included in the adhesive layer in a pharmaceutically effective amount.

An example of a useful commercially available adhesive is DUROTAK 380-2819 available from National Starch, which is a self-crosslinking solution acrylic pressure sensitive adhesive containing 40% by weight solids in a solvent blend of ethyl acetate/isopropanol/heptanes/toluene/pentanedione.

Additional examples of adhesives and aspects thereof which may be suitable for use in the present invention, include those described in U.S. Pat. No. 7,078,582. Specific examples of potentially suitable adhesives include those set forth below and designated as Adhesives A-F.

Adhesive A—Fibers containing polyacrylate pressure sensitive adhesive (PSA) (5-mil thick) (0.13 mm) prepared as described in Example 20 of U.S. patent application Ser. No. 09/764,478 entitled "Pressure Sensitive Adhesives and a Fibrous Reinforcing Material," filed on Jan. 17, 2001, published as 2002/0164446.

Adhesive B—Tackified KRATON pressure sensitive adhesive comprising 50 weight % KRATON 1107 (a styrene-isoprene copolymer thermoplastic elastomer, available from Shell Chemical Co., Houston, Tex.) and 50 weight % ESCOREZ 1310 tackifier (an alphatic resin, available from Exxon Chemical Co., Houston, Tex.); hot melt coated at an 8-mil (0.2 mm) thickness on a standard release liner.

Adhesive C—A pressure sensitive adhesive blend (75/25) of an isoctyl acrylate/acrylic acid pressure sensitive adhesive and KRATON D1107P (styrene-isoprene-stryene block copolymer) prepared as described in Example 1 of International Publication No. WO 96/25469 Hyde et al. The pressure sensitive adhesive was extruded to a thickness of 0.12 mm.

Adhesive D—A multilayer co-extruded pressure sensitive adhesive material made from 61 layers of alternating ABABA, where A is an acrylic pressure sensitive adhesive and B is a hydrophilic polyurethane as described in Example 11 of U.S. Pat. No. 6,045,895 to Hyde et al. Two 0.06 mm thick extruded layers of this pressure sensitive adhesive material were laminated together to provide Adhesive D (0.12 mm thick).

Adhesive E—A multilayer co-extruded pressure sensitive adhesive material made from 61 layers of alternating ABABA, where A is an acrylic pressure sensitive adhesive and B is a polyether-block amide, as described in Example 12 of U.S. Pat. No. 6,045,895 to Hyde et al. Two 0.06 mm thick extruded layers of this pressure sensitive adhesive material were laminated together to provide Adhesive B (0.12 mm thick).

Adhesive F—Fiber-containing polyacrylate pressure sensitive adhesive prepared as described in Example 28 of U.S. patent application Ser. No. 09/764,478, entitled "Pressure Sensitive Adhesives and a Fibrouse Reinforcing Material," filed on Jan. 17, 2001, published as 2002/0164446.

Although pressure sensitive adhesives are preferred, it will be understood that the present invention is not limited to such.

Release Liner

Suitable materials for liners for the preferred laminates such as layer 20 in FIG. 1 and layer 210 in FIG. 6, include those made with kraft papers, polyester, polypropylene (PP), polyethylene (PE) or other composite constructions. The release coatings are preferentially coated with low energy materials like silicone, fluorochemicals, etc. that afford beneficial performance. Examples of representative silicone materials are provided in Chapter 18, Handbook of Pressure Sensitive Adhesives, Van Nostrand Reinhold, 1982, page 384. Examples of suitable fluorochemicals are described in U.S. Pat. No. 4,472,480.

The present invention includes various combinations of these materials. The particular selection and application will be appreciated by those skilled in the art in designing functional laminates using optimum facestock, adhesive and liner combinations.

Test Methods 20 min/24 hr Dwell, 90 Peel Adhesion

To measure adhesion, a laminate construction (facestock and PSA) was die-cut into strips having approximate dimensions of 25×204 mm (1×8 in). The strips were then applied by centering along the lengthwise direction of test panels. The panels were washed with acetone isopropyl alcohol. Each panel was 50×152 mm (2×6 in) and brightly annealed, highly polished stainless steel test or HDPE. The strips were rolled down using a 9.9 kg (4.5 lb.), 5.45 pli 65 shore "A" rubber-faced roller, rolling back and forth once, at a rate of 30 cm/min (12 in/min). The samples were conditioned for 20 minutes or 24 hours in a controlled environment testing room maintained at 21° C. (70° F.) and 50% relative humidity. After conditioning, the test strips were peeled away from the test panel in an Instron Universal Tester according to a modified version of the standard tape method as defined by the Pressure-Sensitive Tape Council, PSTC-1 (rev. 1992), according to Peel Adhesion for Single Coated Tapes 180° Angle, where the peel angle was 90° i.e., perpendicular to the surface of the panel, at a rate of 30 cm/min (12 in/min). A load cell linked to a computer was used to estimate the values reported in N/inch. All tests were conducted in triplicate.

Good wet and dry adhesion levels were also measured for some applications.

Sheffield Smoothness/Air Permeability Test

The surface roughness measure afforded by an appropriately modified Sheffield Smoothness test (TAPPI test method T 538 om-96) is also a good method for evaluating the air sealing or air egress/ingress characteristics of an adhesively adhered article. This measure also provides a relative ranking of the ability to evaluate fluid ingress/egress within a construction using air as the probe. The sample specimens were analyzed using a Hagerty Technologies Model 538 smoothness tester. The range of values measured are 95% confidence interval ranges determined using Student's t-test. A higher value in Sheffield Units indicates a rougher surface thereby displaying greater amounts of fluid egress propensity.

The Air Permeability test is performed using instruments like those available from Frazier Instruments and following the guidelines of ASTM method 3574.

Interfacial Diffusion Rate

Figure 22:
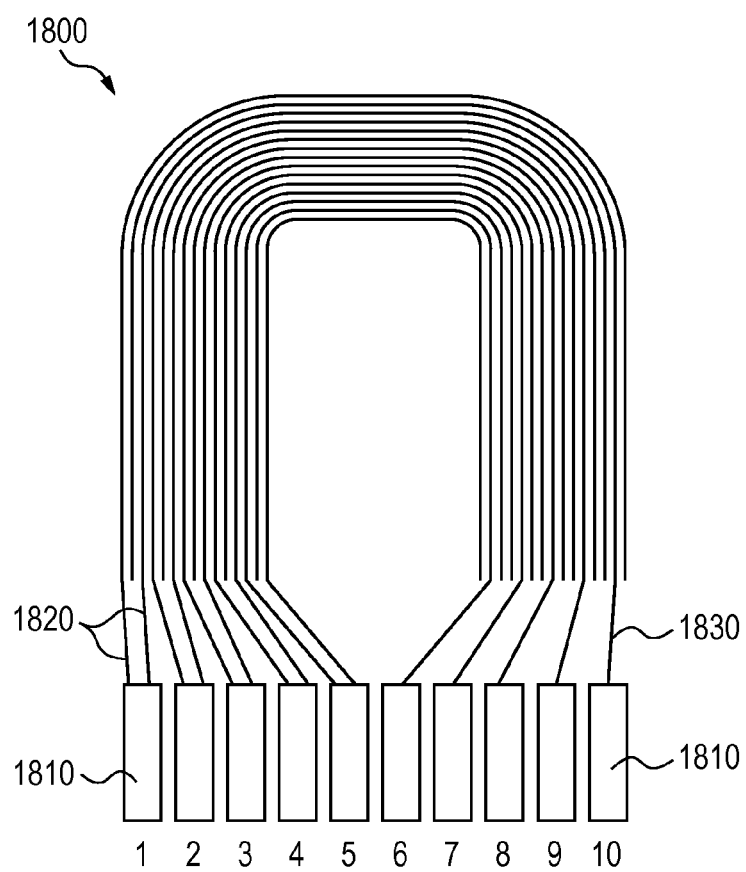
FIG. 22 is an illustration of a component that can be used in testing and analysis of the preferred laminates of the invention.
Figure 23:
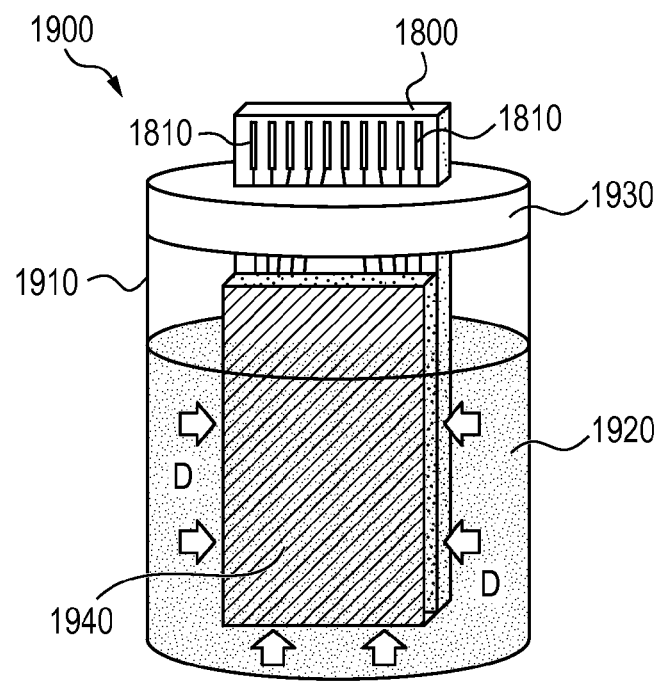
FIG. 23 is a schematic illustration of a testing assembly that can be used in testing and analysis of the preferred laminates of the invention.

A test method that can potentially probe this rate of interfacial diffusion is by the use of single frequency capacitance measurements (SFCM) using a spaced array of interdigitated electrode sensor plates as shown in FIGS. 22 and 23. Details of this test method are provided in "Interfacial Diffusion of Fluids in Pressure Sensitive Adhesives," E. P. O'Brien; T. C. Ward, Journal of ASTM International, 2, 1-8 (2005). Generally, FIG. 22 illustrates an electrode substrate 1800 having a plurality of electrical contacts 1810 and a plurality of spaced, generally parallel electrical traces extending between the contacts, in a U-shaped pattern. Preferably, for a pair of contacts such as contacts designated as "1" and "10," two traces 1820 extend in a parallel fashion towards contact 10. And, a trace 1830 extends from contact 10 between the two traces 1820 towards contact 1.

The fluid under test can be monitored for ingress through edges or lateral regions of an assembly by monitoring change in the measured capacitance using an impedance analyzer. Inspection of a normalized capacitance as a function of time and the spatial resolution of the conductive traces reflects the rate of interfacial diffusion. This data, in turn, can be used to craft the optimum number and spacing of the wells or apertures in the interior layer of the laminates described herein. Too many apertures or wells can compromise the integrity of the laminate and too few wells may not be effective for complete and uniform fluid diffusion. Optical microscopy/image analysis (OM/IA), and Attenuated Total Reflectance Fourier Transform Infrared (ATR-FTIR) are potential alternative techniques of quantifying this. FIG. 23 is a schematic illustration of a representative system 1900 comprising the electrode or trace substrate 1800 having electrical contacts 1810. The electrode substrate 1800 then receives a pressure sensitive tape 1940 which is applied over the interdigitated traces. The electrode and tape assembly is then placed in a container 1910, such as a 40 ml glass vial, and partially submerged in a fluid 1920 as shown in FIG. 23. A fitted cap 1930 such as formed from a silicone rubber is used to close the container, and allow access to the sets of contact pads 1810, for subsequent analysis. As noted, ingress of fluid 1920 in the direction of arrows D can be readily assessed.

Dermal Peels, Stripped Corneocytes & TEWL

Dermal peels may be performed on consenting adults by use of adhesive test strips that are peeled to measure 90° peel adhesions at about 4 inches/min. Details of this test are provided in "Experiments on Peeling Adhesive Tapes from Human Forearms", A. C. Karwoski; R. H. Plaut, Skin research and technology, 10, 271-277 (2004). To measure the amount of stripped corneocytes, the face of the strip is stained with a cationic dye (gentian violet, 1%; brilliant green, 0.5% and distilled water, 98.5%), and the ratio of stripped corneocytes to the total applied area is measured using an optical image analyzer.

At the same applied area, transepidermal water loss (TEWL) and hydration of the stratum corneum can also be measured with TEWAMETER available from (Courage+ Khazaka Electronics GmbH, Germany) and Corneometer CM820 (Courage+ Khazaka) respectively. For details, see "Skin Irritation Due to Repetitive Application of Adhesive Tape; the Influence of Adhesive Strength and Seasonal Variability", F. Tokumura; K. Umekage; M. Sado; S. Otsuka, S. Suda; M. Taniguchi; A. Yamori; A. Nakamura; J. Kawai; K. Ika, Skin Research and Technology, 11, 102-106 (2005).

Moisture Vapor Transmission Rate (MVTR)

The moisture vapor transmission rate (MVTR) is generally expected to be greater than about 300 gms/m$^2$/day as measured by ASTM E 96-80 at 40° C.

Additional Aspects

The following additional aspects may in certain applications, be provided or otherwise utilized in association with the present invention.

Figure 24:
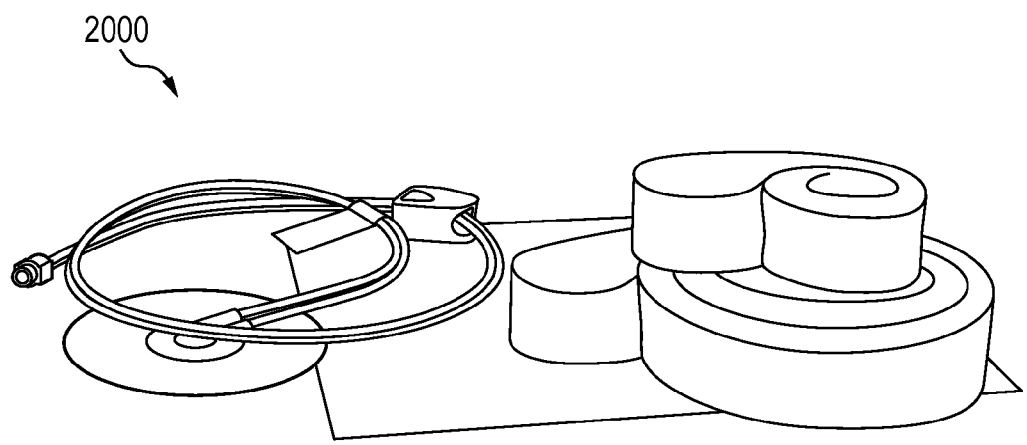
FIG. 24 is an illustration of components typically used in vacuum assisted closure (VAC) therapy, for which certain preferred embodiments of the invention may be suitable.

In one aspect, a micro/macro-needle engineered assembly can be used to quickly and effectively puncture and subsequently seal into a polyurethane foam island used in vacuum assist closure (VAC) therapy. This helps eliminate an operation of cutting a hole with scissors as suggested by 3M in their handling of KCI's SIMPLACE product 2000, as shown in FIG. 24. Thus, in this application, a laminate assembly as described herein for selectively administering an adhesive deactivating agent, is combined with an assembly of microneedles used for sample collection. The plurality of microneedles ensures that a capillary is struck. Such microneedles may be of the type as available from Pelikan of Palo Alto, Calif. and/or Kumetrix of Union City, Calif., or as described in U.S. Pat. No. 6,503,231.

In another aspect, a time indicator is provided which can be used in association with medical dressings and bandages to alarm or notify a nurse or other practitioner to change bandages at appropriate intervals. This can be readily accomplished for example, by color change. Thus, it is contemplated for example that one or more of the preferred laminate assemblies as described herein could be provided with a layer or layer region, viewable from the exterior of the laminate, of a time-based color indicator. Chemical systems that change color over time are well known in the art such as described in U.S. Pat. No. 5,990,199; and U.S. Pat. No. 6,794,318 for example.

In yet another aspect, liquid bandages as known in the art could be dispensed through crushable capsules. Thus, in this version of the present invention, rupturable capsules such as microcapsules, containing a liquid bandage composition are incorporated in a laminate assembly such as described herein. The layer or region of filled capsules is disposed along a face or proximate thereto, which can be placed in contact with a wound area. Upon application of pressure, the microcapsules are ruptured, thereby releasing a flowable liquid bandage composition. Liquid or conformable bandage compositions are well known in the art, such as described in U.S. Pat. Nos. 5,725,491; 4,987,893; 5,103,812; 4,584,192; and US Patent Application Publication 2006/0030808 for example.

In still another aspect, the present invention provides patterning of adhesive to minimize pain. Patterning potentially affords minimizing stress accumulation during peeling due to an irregular peel front. This has been qualitatively confirmed. In such applications involving patterned adhesives, it is contemplated that an apertured layer as described herein could be disposed over or adjacent to the adhesive layer, and the apertures formed in the layer in a similar pattern as that of the adhesive.

Furthermore, it is also contemplated that the present invention could be used in conjunction with adhesive films or layers used for intravenous (IV) catheter fixation or incise film applications.

In many or all of the various embodiments and aspects described herein, it is important that a bacterial barrier be provided. Thus, it is contemplated that appropriate barrier films be utilized or otherwise incorporated in the various laminate assemblies.

In yet another feature in accordance with the present invention, one or more sensors are incorporated into the laminates. It is contemplated that a wide array of sensors, sensor components and related provisions could be incorporated into the multilayer structure to provide information as to the state of a wound or other affected area, conditions of the substrate or skin, conditions or state of the adhesive layer in contact with the skin, and condition of other layers in the laminate. For example, sensors could be incorporated in the laminate that monitor or report (e.g. record & transmit data using technologies like integrated RFID) the state of the wound such as for example, assessing the level of protease ingressing into the pen-wound area sensors. Other relevant parameters may include any combination of wound status feedback including skin temperature, infection level, swelling, symptomatic coloration, histamine or heparin levels, etc.

Many other benefits will no doubt become apparent from future application and development of this technology.

All patents, published applications, and articles noted herein are hereby incorporated by reference in their entirety.

Furthermore, it will be understood that any one or more features, details or aspects of one embodiment described herein, may be combined with one or more other features, details or aspects of other embodiment(s) described herein. In no way is the present invention limited to any one particular embodiment described herein.

As described hereinabove, the present invention solves many problems associated with previous type devices and methodologies. However, it will be appreciated that various changes in the details, materials and arrangements of components, which have been herein described and illustrated in order to explain the nature of the invention, may be made by those skilled in the art without departing from the principle and scope of the invention, as expressed in the appended claims.

What is claimed is:

1. A multilayer laminate that is adherable to a substrate and selectively releasable therefrom upon application of an agent to an outer face or perimeter of the laminate and appropriate contacting between the agent and the adhesive, the laminate comprising:
an interior layer defining a plurality of fluid passageway conduits or apertures extending through the interior layer, the interior layer exhibiting a controllable flow profile across the thickness of the interior layer, the interior layer defining a bottom surface and an oppositely directed top surface;
an adhesive layer disposed along the bottom surface of the interior layer, wherein the adhesive layer includes channels incorporated in the adhesive layer of the multilayer laminate which allow for rapid ingress of an adhesive deactivating agent;
a carrier layer is disposed on the top surface of the interior layer;
wherein upon contacting the adhesive layer to the substrate, the laminate is adhesively adhered thereto; upon removal of the cover layer from the laminate, the interior layer and plurality of fluid passageway conduits are exposed; and upon application of an effective amount of the agent to the top surface of the interior layer, transport of the agent to the adhesive, and passage of sufficient contact time between the agent and the adhesive, the adhesively adhered laminate can be easily removed from the substrate.

2. The multilayer laminate of claim 1 wherein the adhesive of the laminate has a tackiness that decreases after the agent is applied.

3. The multilayer laminate of claim 1, wherein the conduits defined in the interior layer have diameters that range from about 0.5 mils to about 2000 mils.

4. The multilayer laminate of claim 1, wherein the interior layer includes a plurality of apertures, perforations, slits, pores or combinations thereof that enable controlled passage of one or more agents from one face of the layer through another face of the layer.

5. The multilayer laminate of claim 1, wherein the agent is an adhesive deactivating agent and is selected from the group consisting of silicones, perfluoroalkyl derivatives, low molecular weight oils, aqueous compositions, alkyl esters, limonene derivatives, paraffin solvents, hydrocarbon solvents, alkyl ethers, aromatic esters, surfactants, and combinations thereof.

6. The multilayer laminate of claim 1, wherein the number of conduits or apertures range from about 5 to about 500 per square inch of layer.

7. The multilayer laminate of claim 1, wherein the agent includes a medicant-like anesthetic, analgesic, cooling/heating agent or combination thereof.

8. The multilayer laminate of claim 1, wherein the agent is applied via a means selected from the group consisting of a secondary carrier device, a skin barrier-like application, an individually sterile packed dispenser or spray, an impregnated gauze/foam carrier, and an encapsulated release on demand medium to measure out needed amounts.

9. The multilayer laminate of claim 1, wherein the adhesive layer includes a pressure sensitive adhesive.

10. The multilayer laminate of claim 1, wherein the agent includes a component for coating hair to eliminate hair pull induced pain during removal of the laminate.

11. The multilayer laminate of claim 1, wherein the adhesive layer comprises a pattern of adhesive.

12. The multilayer laminate of claim 1, wherein the laminate further comprises a sensor incorporated into the laminate to provide information as to the state of a wound or other affected area.

13. The multilayer laminate of claim 1, wherein the interior layer is in the form of an infraction layer.

14. The multilayer laminate of claim 1, wherein the interior layer includes a region of ink conduits for facilitating fluid flow through the interior layer.

15. A system for selectively adhering and selectively releasing a multilayer laminate to and from a substrate, the system comprising:
a multilayer laminate comprising (i) an interior layer defining a plurality of fluid passageway conduits or apertures extending through the interior layer, the interior layer exhibiting a controllable flow profile across the thickness of the interior layer, the interior layer defining a bottom face and an oppositely directed top face, (ii) an adhesive layer disposed along the bottom face of the interior layer, and (iii) a cover layer disposed on the top face of the interior layer;

an adhesive deactivating agent;

wherein upon contacting the adhesive layer to the substrate, the laminate is adhesively adhered thereto; upon removal of the cover layer from the laminate, the interior layer and plurality of fluid passageway conduits are exposed; and upon application of an effective amount of the adhesive deactivating agent to the top face of the interior layer and passage of sufficient contact time between the adhesive deactivating agent and the adhesive, the adhesively adhered laminate can be easily removed from the substrate.

16. The system of claim 15, wherein the adhesive of the laminate has a tackiness that decreases after the adhesive deactivating agent is applied.

17. The system of claim 15, wherein the conduits defined in the interior layer have diameters that range from about 0.5 mils to about 2000 mils.

18. The system of claim 15, wherein the laminate is incorporated in a medical product selected from the group consisting of bandages, dressings, gauze, tape, wound closure covers, closure strips, and pads.

19. The system of claim 15, wherein the interior layer includes a plurality of apertures, perforations, slits, pores or combinations thereof that enable controlled passage of one or more agents from one face of the layer through another face of the layer.

20. The system of claim 15, wherein the adhesive deactivating agent is selected from the group consisting of silicones, perfluoroalkyl derivatives, low molecular weight oils, aqueous compositions, alkyl esters, limonene derivatives, paraffin solvents, hydrocarbon solvents, alkyl ethers, aromatic esters, surfactants, and combinations thereof.

21. The system of claim 15, wherein the number of conduits or apertures range from about 5 to about 500 per square inch of layer.

22. The system of claim 15, wherein the adhesive deactivating agent includes a medicant-like anesthetic, analgesic, cooling/heating agent or combination thereof.

23. The system of claim 15, wherein the adhesive deactivating agent is applied via a means selected from the group consisting of a secondary carrier device, a skin barrier-like application, an individually sterile packed dispenser or spray, an impregnated gauze/foam carrier, and an encapsulated release on demand medium to measure out needed amounts.

24. The system of claim 15, wherein the adhesive layer includes a pressure sensitive adhesive.

25. The system of claim 15, wherein the adhesive layer includes channels incorporated in the adhesive layer of the multilayer laminate which allows for rapid ingress of the adhesive deactivating agent.

26. The system of claim 15, wherein the adhesive layer comprises a pattern of adhesive.

27. The system of claim 15, wherein the multilayer laminate further comprises a sensor incorporated into the laminate to provide information as to the state of a wound or other affected area.

28. The system of claim 15, wherein the adhesive deactivating agent is in the form of a spray, wipe, sterile pad or combinations thereof.

29. The system of claim 15, wherein the interior layer is in the form of an infraction layer.

30. The system of claim 15, wherein the interior layer includes a region of ink conduits for facilitating fluid flow through the interior layer.

31. A method for selectively adhering a multilayer laminate to and from a substrate, the method comprising the steps of:

providing a multilayer laminate comprising (i) an interior layer defining a plurality of fluid passageway conduits or apertures extending through the interior layer, the interior layer exhibiting a controllable flow profile across the thickness of the interior layer, the interior layer defining a bottom surface and an oppositely directed top surface; (ii) an adhesive layer disposed along the bottom surface of the interior layer; (iii) a carrier layer disposed on the top surface of the interior layer; and (iv) a release liner in contact with the adhesive layer;

removing the release liner from the adhesive layer of the multilayer laminate to thereby expose the adhesive layer;

applying the multilayer laminate onto the substrate;

removing the carrier layer to thereby expose the interior layer;

applying an effective amount of an adhesive deactivating agent onto the interior layer, whereby the agent travels through the interior layer and after sufficient contact time between the agent and the adhesive, the laminate can be easily removed from the substrate.

32. The method of claim 31, wherein the multilayer laminate also comprises (v) an outer cover layer disposed adjacent the carrier layer.

33. The method of claim 31, wherein the adhesive of the laminate has a tackiness that decreases after the adhesive deactivating agent is applied.

34. The method of claim 31, wherein the conduits defined in the interior layer of the laminate have diameters that range from about 0.5 mils to about 2000 mils.

35. The method of claim 31, wherein the interior layer of the laminate includes a plurality of apertures, perforations, slits, pores or combinations thereof that enable controlled passage of one or more agents from one face of the layer through another face of the layer.

36. The method of claim 31, wherein the adhesive deactivating agent is selected from the group consisting of silicones, perfluoroalkyl derivatives, low molecular weight oils, aqueous compositions, alkyl esters, limonene derivatives, paraffin solvents, hydrocarbon solvents, alkyl ethers, aromatic esters, surfactants, and combinations thereof.

37. The method of claim 31, wherein the number of conduits or apertures in the interior layer of the laminate range from about 5 to about 500 per square inch of layer.

38. The method of claim 31, wherein the adhesive deactivating agent includes a medicant-like anesthetic, analgesic, cooling/heating agent or combination thereof.

39. The method of claim 31, wherein the adhesive deactivating agent is applied via a means selected from the group consisting of a secondary carrier device, a skin barrier-like application, an individually sterile packed dispenser or spray, an impregnated gauze/foam carrier, and an encapsulated release on demand medium to measure out needed amounts.

40. The method of claim 31, wherein the adhesive layer includes a pressure sensitive adhesive.

41. The method of claim 31, wherein the adhesive layer includes channels incorporated in the adhesive layer of the multilayer laminate which allows for rapid ingress of the adhesive deactivating agent.

42. The method of claim 31, wherein the adhesive layer comprises a pattern of adhesive.

43. The method of claim 31, wherein the multilayer laminate further comprises a sensor incorporated into the laminate to provide information as to the state of a wound or other affected area.

44. The method of claim 31, wherein the laminate is incorporated in a medical product selected from the group consisting of bandages, dressings, gauze, tape, wound closure covers, closure strips, and pads.

45. The method of claim 31, wherein the interior layer is in the form of an infraction layer.

46. The method of claim 31, wherein the interior layer includes a region of ink conduits for facilitating fluid flow through the interior layer.

47. A method for selectively adhering a multilayer laminate to a substrate and wound bed utilizing a vacuum assisted closure therapy; the method comprising the steps of:
   providing a multilayer laminate comprising (i) an interior layer defining a plurality of fluid passageway conduits or apertures extending through the interior layer, the interior layer exhibiting a controllable flow profile across the thickness of the interior layer, the interior layer defining a bottom surface and an oppositely directed top surface; (ii) an adhesive layer disposed along the bottom surface of the interior layer; (iii) a carrier layer disposed on the top surface of the interior layer; and (iv) a release liner in contact with the adhesive layer;
   placing a piece of thick material that is sized and configured to cover the wound bed, over the wound bed;
   peeling off the release liner from the adhesive layer of the multilayer laminate;
   applying the multilayer laminate over the wound bed;
   forming a hole in the multilayer laminate;
   applying a pad adapted for vacuum connection over the hole in the multilayer laminate; and
   connecting a vacuum source to the pad through the hole in the multilayer laminate.

48. The method of claim 47, wherein the multilayer laminate also comprises (v) an outer cover layer disposed adjacent the carrier layer.

49. The method of claim 47, wherein the pad includes associated tubing for connection to the vacuum source.

50. The method of claim 48, wherein the pad is in contact with the outer cover layer.

51. The method of claim 47, further comprising:
   selectively releasing the multilayer laminate from the substrate and wound bed.

52. The method of claim 51, wherein the selective releasing is performed by treating the multilayer laminate with an adhesive deactivating agent.

53. The method of claim 52, wherein the adhesive deactivating agent is selected from the group consisting of silicones, perfluoroalkyl derivatives, low molecular weight oils, aqueous compositions, alkyl esters, limonene derivatives, paraffin solvents, hydrocarbon solvents, alkyl ethers, aromatic esters, surfactants, and combinations thereof.

54. The method of claim 52, wherein the adhesive deactivating agent includes a medicant-like anesthetic, analgesic, cooling/heating agent or combination thereof.

55. The method of claim 52, wherein the adhesive deactivating agent is applied via a means selected from the group consisting of a secondary carrier device, a skin barrier-like application, an individually sterile packed dispenser or spray, an impregnated gauze/foam carrier, and an encapsulated release on demand medium to measure out needed amounts.

56. The method of claim 47, further comprising:
   selectively releasing the multilayer laminate from the substrate and the wound bed by removing the pad and the multilayer laminate.

57. The method of claim 56, wherein the selective releasing is performed by treating the multilayer laminate with an adhesive deactivating agent.

58. The method of claim 47, wherein the adhesive of the laminate has a tackiness that decreases after an adhesive deactivating agent is applied.

59. The method of claim 47, wherein the conduits defined in the interior layer of the laminate have diameters that range from about 0.5 mils to about 2000 mils.

60. The method of claim 47, wherein the interior layer of the laminate includes a plurality of apertures, perforations, slits, pores or combinations thereof that enable controlled passage of one or more agents from one face of the layer through another face of the layer.

61. The method of claim 47, wherein the number of conduits or apertures in the interior layer of the laminate range from about 5 to about 500 per square inch of layer.

62. The method of claim 47, wherein the adhesive layer includes a pressure sensitive adhesive.

63. The method of claim 47, wherein the adhesive layer includes channels incorporated in the adhesive layer of the multilayer laminate which allows for rapid ingress of the adhesive deactivating agent.

64. The method of claim 47, wherein the adhesive layer comprises a pattern of adhesive.

65. The method of claim 47, wherein the multilayer laminate further comprises a sensor incorporated into the laminate to provide information as to the state of a wound or other affected area.

66. The method of claim 47, wherein the laminate is incorporated in a medical product selected from the group consisting of bandages, dressings, gauze, tape, wound closure covers, closure strips, and pads.

67. The method of claim 47, wherein the interior layer is in the form of an infraction layer.

68. The method of claim 47, wherein the interior layer includes a region of ink conduits for facilitating fluid flow through the interior layer.

* * * * *